US007313482B2

(12) United States Patent
Drlica et al.

(10) Patent No.: US 7,313,482 B2
(45) Date of Patent: Dec. 25, 2007

(54) SELECTION OF TARGET SITES FOR ANTISENSE ATTACK OF RNA

(75) Inventors: Karl Drlica, New York, NY (US); Jian-Ying Wang, Piscataway, NJ (US)

(73) Assignee: The Public Health Research Institute of the city of New York, Inc., Newark, NJ (US)

( * ) Notice: Subject to any disclaimer, the term of this patent is extended or adjusted under 35 U.S.C. 154(b) by 46 days.

(21) Appl. No.: 10/478,049

(22) PCT Filed: May 15, 2002

(86) PCT No.: PCT/US02/18532

§ 371 (c)(1),
(2), (4) Date: Apr. 29, 2004

(87) PCT Pub. No.: WO02/095059

PCT Pub. Date: Nov. 28, 2002

(65) Prior Publication Data

US 2004/0236517 A1 Nov. 25, 2004

Related U.S. Application Data

(60) Provisional application No. 60/291,737, filed on May 17, 2001.

(51) Int. Cl.
*G01N 33/48* (2006.01)
*G01N 33/00* (2006.01)
*C12Q 1/00* (2006.01)
*C12Q 1/68* (2006.01)

(52) U.S. Cl. .................. 702/19; 435/4; 435/6; 702/20; 702/27

(58) Field of Classification Search ..................... None
See application file for complete search history.

(56) References Cited

FOREIGN PATENT DOCUMENTS

EP 1 103910 A1 5/2001

OTHER PUBLICATIONS

Birikh, K. R., Y. A. Berlin, H. Soreq, and F. Eckstein. (1997) Probing accessible sites for ribozymes on human acetylcholinesterase RNA. *RNA* 3: 429-437.

Christofferson, R. E., J. McSwiggen, and D. Konings. (1994) Application of computational technologies to ribozyme biotechnology products. *Journal of Molecular Structure* (Theochem)311: 273-284.

Ding, Y., and C. E. Lawrence. (2001) Statistical prediction of single-stranded regions in RNA secondary structure and application to predicting effective antisense target sites and beyond. *Nucleic Acids Res* 29: 1034-46.

Kushon, Stuart A. et al., (2001) Effect of Secondayr Structure on the Thermodynamics and Kinetics of PNA Hybridization to DNA Hairpins. *J. Am. Chem. Soc.* 123; 10805-10813.

Luebke, K. J., R. P. Balog, and H. R. Garner. (2003) Prioritized selection of oligodeoxyribonucleotide probes for efficient hybridization to RNA transcripts. *Nucleic Acids Res* 31: 750-8.

Mathews, D. H., M. E. Burkard, S. M. Freier, J. R. Wyatt, and D. H. Turner. (1999) Predicting oligonucleotide affinity to nucleic acid target. *RNA* 5: 1458-1469.

Matveeva, O. V., A. D. Tsodikov, M. Giddings, S. M. Freier, J. R. Wyatt, A. N. Spiridonov, S. A. Shabalina, R. F. Gesteland, and J. F. Atkins (2000) Identification of sequence motifs in olionucleotides whose presence is correlated with antisense activity. *Nucleic Acids Res* 28: 2862-2865.

Patzel, V. et al. (2000) In vitro selection supports the view of a kinetic control of antisense RNA-mediated inhibition of gene expression in mammalian cells. *Nucleic Acids Res* 28; 2462-2466.

Patzel, V., and G. Sczakiel. (2000) In vitro selection supports the view of a kinetic control of antisense RNA-mediated inhibition of gene expression in mammalian cells. *Nucleic Acids Res*28: 2462-2466.

Scherr, M., J. J. Rossi, G. Sczakiel, and V. Patzel. (2000) RNA accessibility prediction: a theoretical approach is consistent with experimental studies in cell extracts. *Nucleic Acids Res* 28:2455-2461.

Stull, R. A., L. A. Taylor, and J. Francis C. Szoka. (1992) Predicting antisense oligonucleotide inhibitory efficacy: a computational approach using histograms and thermodynamic indices. *Nucleic Acids Research* 20: 3501-3508.

Tu, G. C., Q. N. Cao, F. Zhou, and Y. Israel. (1998) Tetranucleotide GGGA motif in primary RNA transcripts. Novel target site for antisense design. *J Biol Chem* 273: 25125-31.

Walton, S. P., G. N. Stephanopoulos, M. L. Yarmush, and C. M. Roth. (1999) Prediction of antisense oligonucleotide binding affinity to a structured RNA target. *Biotechnology and Bioengineering* 65: 1-9.

Walton, S.P., et al. (2002) Thermodynamic and Kinetic Characterization of Antisense Oligodeoxynucleotide Binding to a Structured mRNA. *Biophysical Journal* 82; 366-377.

Wang, J.-Y., and K. Drlica. (2003) Modeling hybridization kinetics. *Mathematical Biosciences* 183: 37-47.

Patzel, V., and G. Sczakiel. (1999) Length Dependence of RNA-RNA Annealing. J. Mol. Biol. (1999) 294, 1127-1134.

*Primary Examiner*—Ram R. Shukla
*Assistant Examiner*—Eric S DeJong
(74) *Attorney, Agent, or Firm*—Licata & Tyrrell P.C.

(57) ABSTRACT

Nucleic acid hybridization under steady-state conditions is described by a kinetic model in which the intermediate state is assumed to be locally single stranded. An expression was derived that relates nucleic acid secondary structure to the rate of oligonucleotide-RNA hybridization. The model allows the calculation of a rate factor that is proportional to the rate constant for hybridization between complementary nucleic acids and is generally applicable to any RNA molecule with potential utility for rapid identification of sites for antisense attack of mRNA.

2 Claims, 15 Drawing Sheets

Rate Factc
1.0E+7
1.0E+5
1.0E+3
1.0E+1
1.0E-1
1.0E-3
50
60
70
80
90
100
110
Anealing Rate
1.0E+5
1.0E+4
1.0E+3
1.0E+2
1.0E+1
Antisense Length Log x
-3
1
5
9
a 1 2 3 4 5 6 7 8 9 10 11 12 13 14 15 16 b a 17 18 19 20 21 22 23 24 25 26 27 28 29 30 31 32

SEQUENCE LISTING

<160> NUMBER OF SEQ ID NOS: 26

<210> SEQ ID NO 1
<211> LENGTH: 101
<212> TYPE: RNA
<213> ORGANISM: Artificial Sequence
<220> FEATURE:
<223> OTHER INFORMATION: Synthetic oligonucleotide

<400> SEQUENCE: 1
gcggccgacg aacaauguca ccuuauugac auugaugugu uauaacuuac agaucucuag 60
caguggcgcc cgaacaggga ccugaaagcu aaagggaagc u 101

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
gacattgttc gtcggccgc 19

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 3
catcaatgtc aataaggtga cattgttcg 29

<210> SEQ ID NO 4
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 4
tgctagagat ctctaagtta taacacatca atgtcaa 37

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
ggcgccactg ctagagatct ctaagttata 30

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
gtccctgttc gggcgcc 17

-continued

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
agcttccctt tcgctttcag gtc 23

<210> SEQ ID NO 8
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 8
ctgcaggaat tctaatacga ctcactatag cttttagtca gtgtggaaaa tctctagc 58

<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 9
ctgcaggaat tcgcactcaa ggcaagcttt attgaggctt 40

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ctgctatgtc gacacccaat 20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gtctaggatc tactggctcc 20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gttttaggct gacttcctgg 20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide -continued

<400> SEQUENCE: 13
aaacaaactt ggcaatgaaa 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tgcttccagg gctctagtct 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
gagctcctct ggtttccctt 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
ctactggctc catttcttgc 20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
ttttacaata gcaattggta 20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ttgttatgaa acaaacttgg 20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aggagatgcc taaggctttt 20

-continued

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gatctgtctc tgtctctctc 20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ccacctcctc ctcctcttgt 20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ttattcttct aggtatgtgg 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
caggcacaag cagcattggt 20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
atctgacccc tggccctggt 20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tagcttgtag caccatccaa 20

<210> SEQ ID NO 26
<211> LENGTH: 20
<212> TYPE: DNA
<213> ORGANISM: Artificial Sequence -continued

```
<220> FEATURE:
<223> OTHER INFORMATION: Synthetic oligonucleotide

<400> SEQUENCE: 26

cttacactgc cattgctaca                                                    20
```

SELECTION OF TARGET SITES FOR ANTISENSE ATTACK OF RNA

This application is a national stage entry under 35 U.S.C. 371 of International Application PCT/US02/18532 filed May 15, 2002 and United States Provisional application 60/291,737 filed May 17, 2001.

STATEMENT AS TO FEDERALLY SPONSORED RESEARCH

This invention was made with Government support under Grant CA72860 awarded by the National Institutes of Health. The Government may have certain rights in the invention.

FIELD OF THE INVENTION

This invention relates to methods and devices for estimating initial rates, predicting nucleation sites, and selecting sites accessible for antisense attack of RNA.

BACKGROUND OF THE INVENTION

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, Vitravene® (for treatment of cytomegalovirus retinitis), reflecting that antisense has therapeutic utility.

A recently identified application for antisense ODNs is targeted disruption of expression of genes having unknown function. The nucleotide sequence of all genes of many species, including human, is becoming available to the research community, but the function of only a fraction is known. The widespread application of gene chip arrays will allow hypotheses to be developed about gene circuitry, and antisense ODNs will make it possible to test these hypotheses by down regulation of specific genes singly and in combination. The use of antisense ODNs is expected to increase as genomic nucleotide sequences become available for more organisms and as more pharmaceutical companies use this information to seek new drugs.

Widespread use of antisense nucleic acids nonetheless faces a serious obstacle. Extensive RNA structure that impedes antisense-RNA hybridization makes it difficult to identify favorable sites in a target RNA for antisense binding. Since equilibrium is unlikely to be achieved inside cells, understanding hybridization is likely to require an accurate description of hybridization rate. The challenge is substantial because hybridization rate can be very fast even though RNAs are expected to contain considerable secondary structure. For example, in *Escherichia coli* regulatory antisense RNAs form stable complexes with their target RNA at second order association rates that are close to the upper limit for unstructured RNA association ($10^6$ $M^{-1}sec^{-1}$; Persson et al., 1988; Porschke and Eigen, 1971; Tomizawa, 1984)).

Previous efforts to describe hybridization between oligonucleotides and target RNA fall roughly into two groups. In one, predictions of RNA secondary structure were used to identify regions likely to be single stranded and presumably accessible for hybridization (Christofferson et al., 1994; Patzel et al., 1999). Correlation with oligonucleotide hybridization showed considerable scatter, and we now know that single-stranded regions, identified by nucleases, do not correspond to those that hybridize most readily (see FIG. 3 in Birikh et al., 1997). In the second approach, overall energy gain due to hybrid formation was calculated (Stull et al., 1992). This method, which focuses on equilibrium yield of hybrids, provided a poor correlation between energy gain and hybridization of antisense oligonucleotides to RNA (Stull et al., 1992). More recently, Mathews et al. analyzed two experiments (Mathews et al. 1999a). The data from one correlated with the equivalent of $\Delta G_d$ (FIG. 1) while the data of the other correlated with the equivalent of $\Delta G_h$ (FIG. 1). Thus, no general treatment has been available, making it necessary to identify favorable sites for antisense attack of mRNA experimentally (Birikh et al., 1997; Branch, 1998).

A current procedure used to identify such favorable sites involves construction of random sequence ODN libraries, expression and purification of target mRNA, hybridization of library ODNs to target RNA, cleavage of hybrids with RNase H, gel electrophoresis of cleavage products to determine their sizes, and primer extension to accurately determine the cleavage sites. For most laboratories interested in gene function, this procedure for identifying favorable sites for hybridization is a project unto itself A need exists, therefore, for accurate but less time- and labor-intensive methods for identifying favorable sites for hybridization.

SUMMARY OF THE INVENTION

The invention is based on our development of a selection method that makes it possible to calculate a rate factor that is proportional to hybridization rate for all sites in RNA under quasi steady-state conditions. The method of this invention provides a mathematical description of the first step of complementary nucleic acid annealing that can be used to estimate initial rates, predict nucleation sites, and select sites accessible for antisense attack of RNA. A distinctive feature of the method of this invention is that it identifies favorable target sites by using two particular parameters. Our invention relates the overall steady-state rate constant to the melting energy that must be overcome to form a hybrid and to the free energy that is gained as a result of hybrid formation. RNA secondary structure, which is expected to impede binding of oligonucleotides to long RNA targets (Campbell et al., 1997; Lima et al., 1992), is taken into account by using commercially available RNA structure algorithms to calculate melting energy and energy gain. Using the method according to this invention, calculating a rate factor for hybridization to any target site is relatively straightforward.

In general, the invention features a method for calculating a rate factor, which is proportional to initial rate, for hybridization to an RNA molecule by a given antisense nucleic acid. The method includes the steps of calculating the melting energy ($\Delta G_m$) required to convert specific regions of the RNA molecule to a single-stranded state; calculating the energy gain ($\Delta G_d$) resulting from hybridization of said specific regions of said RNA molecule to an oligonucleotide; and calculating rate factor x, where $$x = -\frac{1}{Ce^{\Delta G}m/RT + e^{\Delta}G_d/RT}$$

(for intracellular hybridization) or $$x = \frac{1}{(Ce^{\Delta G}m/RT + e^{\Delta G}d/RT) + [S]}$$

(for single-tube assays).

In one embodiment, the invention features a method for predicting inhibition of intracellular gene expression by a given antisense ribonucleic acid endogenously expressed. The method includes calculating the rate factor x for hybridization to RNA by said endogenously expressed antisense ribonucleic acid using the method described above, with $$x = \frac{1}{Ce^{\Delta G}m/RT + e^{\Delta}G_d/RT}.$$

In another embodiment, the invention features a method for identifying at least one likely nucleation site for RNA-RNA annealing. The method includes the step of calculating in a stepwise manner rate factor x for each short pairing regions (11 to 20 nucleotides long) in an RNA molecule using the method described above, with $$x = \frac{1}{Ce^{\Delta G}m/RT + e^{\Delta}G_d/RT};$$

and identifying a region or regions that has or have maximal values of rate factor x, that region or those regions being the at least one likely nucleation site for RNA-RNA annealing.

In still another embodiment, the invention features a method for identifying accessible sites on an RNA molecule for hybridization by antisense deoxyribonucleic acid. The method includes the steps of calculating in a stepwise manner rate factor x for each short region (11 to 20 nucleotides long) of the antisense deoxyribonucleic acid using the method described above, with $$x = \frac{1}{Ce^{\Delta G}m/RT + e^{\Delta}G_d/RT};$$

and identifying the regions having largest rate factors, those sites being the most accessible sites. An antisense ribonucleic acid suitable for hybridization to a site identified using this method is also contemplated to be an aspect of the invention.

The invention also includes certain devices. One device of the invention is a device for estimating initial rates of attack of RNA by a given antisense ribonucleotide. The device includes a computer having a program that estimates free energy of the secondary structure of the RNA and calculates the rate factor x for hybridization of said RNA to the antisense ribonucleotide according to the method described above, the initial rate of attack being proportional to the rate factor x.

Another device of the invention is a device for identifying nucleation sites for RNA-RNA annealing. The device includes a computer having a program that carries out the method described above for identifying at least one likely nucleation site for RNA-RNA annealing.

Still another device of the invention is a device for identifying accessible sites on an RNA molecule for attack by antisense deoxynucleotides. The device includes a computer having a program that carries out the method described above for identifying accessible sites on an RNA molecule for hybridization by antisense deoxyribonucleic acid.

Yet another embodiment of the invention features a method for estimating melting energy required for freeing a short region of single-stranded RNA from secondary structure within a large RNA. The method includes the steps of using an RNA folding program (e.g., FOLDRNA of the GCG package, which estimates free energy of RNA secondary structure) to determine the free energy of the RNA when said short region of RNA is forced to be single stranded, and using that information to estimate the melting energy required for freeing said short region of RNA from secondary structure, the melting energy being related to the $\Delta G_m$ according to the equation:

$$\Delta G_m = (G_{1anti} + G_{1target}) - (G_{0anti} + G_{0target}).$$

Still another embodiment of the invention features a method for determining at least one function of a gene. The method includes the steps of determining the sequence of the gene; using the method described above for identifying accessible sites on an RNA molecule for hybridization by antisense deoxyribonucleic acid to identify at least one accessible site on an RNA molecule encoded by the gene; synthesizing at least one antisense nucleotide suitable for attacking the identified site; contacting a cell with the synthetic nucleotide; and identifying an effect of the contacting step to determine the function of the gene.

In yet another embodiment still, the invention features a method for developing a drug that targets a specific gene. The method includes the following steps: 1) determining the sequence of the gene; 2) using the method described above for identifying accessible sites on an RNA molecule for hybridization by antisense deoxyribonucleic acid to identify at least one accessible site on an RNA molecule encoded by the gene; and 3) synthesizing a drug suitable for targeting the site.

For antisense, nuclease-resistant oligonucleotides (e.g., phosphorothioates or 2'-O-methylribonucleosides) are generally preferred. Phosphothioates can be used, for example, to keep the intracellular nucleases from rapidly chewing up the antisense molecules. Accordingly, although oligodeoxynucleotides (ODNs) are referred to throughout this application for simplicity and illustrative purposes, both known and yet-to-be discovered nuclease-resistant oligonucleotides can be substituted for ODNs in all of the claimed methods.

The invention offers numerous advantages. By enabling the calculation of relative hybridization rates, the invention enables identification of sites in an RNA target that will hybridize most rapidly with antisense oligonucleotides. Kinetic description of hybridization using the invention makes it possible to identify favorable sites, thereby bypassing certain expensive and time-consuming experimental procedures currently employed. We believe that actively growing and metabolizing cells are effectively modeled using steady-state rate assumptions. Using equilibrium assumptions, resting cells can be modeled. Therefore, the invention is believed to be applicable to both growing and resting cells when parameters are appropriately adjusted.

The widespread application of antisense technology has been constrained by the resources required to discover effective antisense sequences. Advantageously, the present invention can be used to quickly identify the most favorable sites for hybridization of antisense oligonucleotides to any RNA whose nucleotide sequence is known.

In addition to its use in identifying favorable target sites, embodiments of the invention minimize negative effects arising from surrounding sequences. When a vector or a chromosomal gene endogenously expresses antisense RNA, the RNA will almost always be surrounded by extraneous sequences originating from the vector or chromosome. These extraneous sequences can form secondary structures with the antisense sequence and interfere with binding of antisense to the target RNA. The method of this invention can easily take these extra sequences into account during calculation of the rate factor. Thus, the invention is useful in vector design.

The invention can also be applied to catalytic antisense agents such as ribozymes, which bind to their targets by hybridization. Although the internal structures of ribozymes can introduce additional complexities into the analysis, ribozyme kinetics measured in vitro (Campbell et al., 1997) can be closely modeled using the method of this invention (FIG. 2).

An improved ability to identify favorable target sites should encourage more intensive effort to develop antisense-based antiviral therapies (e.g., to reduce infection and to speed patient recovery).

The new methods can advantageously be used to provide whole genome antisense libraries. Such libraries are useful, for example, for determining the function of discovered genes of unknown activity by screening for antisense oligonucleotides that are able to block specific functions. For instance, an antisense genome library can be tested for those sequences that are able to overcome resistance of a primary tumor cell line to a chemotherapeutic agent. This embodiment aids in validating potential targets, or sets of targets, for small molecule drug discovery, and in addition provides a direct route to antisense therapy.

Antisense oligonucleotides selected using this invention can be used to validate a potential drug target by demonstrating the effect of blocking the action of a particular protein (in this case by blocking its expression) prior to investing significant money in a chemistry effort. Furthermore, for certain indications (e.g., topical indications, selected systemic infections, and tumors), antisense oligonucleotides selected using this invention can be used not only to validate a target, but, in the appropriate vector, to treat it.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The binding of an antisense nucleotide to an RNA target, followed by the subsequent destruction or a conformational change of the target, can be described by:

$$A + S \underset{k_{-1}}{\overset{k_1}{\rightleftharpoons}} AS \overset{k_2}{\rightarrow} P, \quad (1)$$

where A is an antisense oligonucleotide, S is the target RNA, AS is the antisense nucleotide-target RNA hybrid, P represents the products of the second step, $k_1$ and $k_{-1}$ are the rate constants for binding and dissociation, respectively, and $k_2$ is the rate constant of the second step, which is assumed to be irreversible. The second step can entail, for example, an enzymatic cleavage, as in the case of antisense DNA-mediated RNase H cleavage reactions, or a structural change, as in the case of full-length annealing of long antisense target RNA hybridization.

Figure 1:
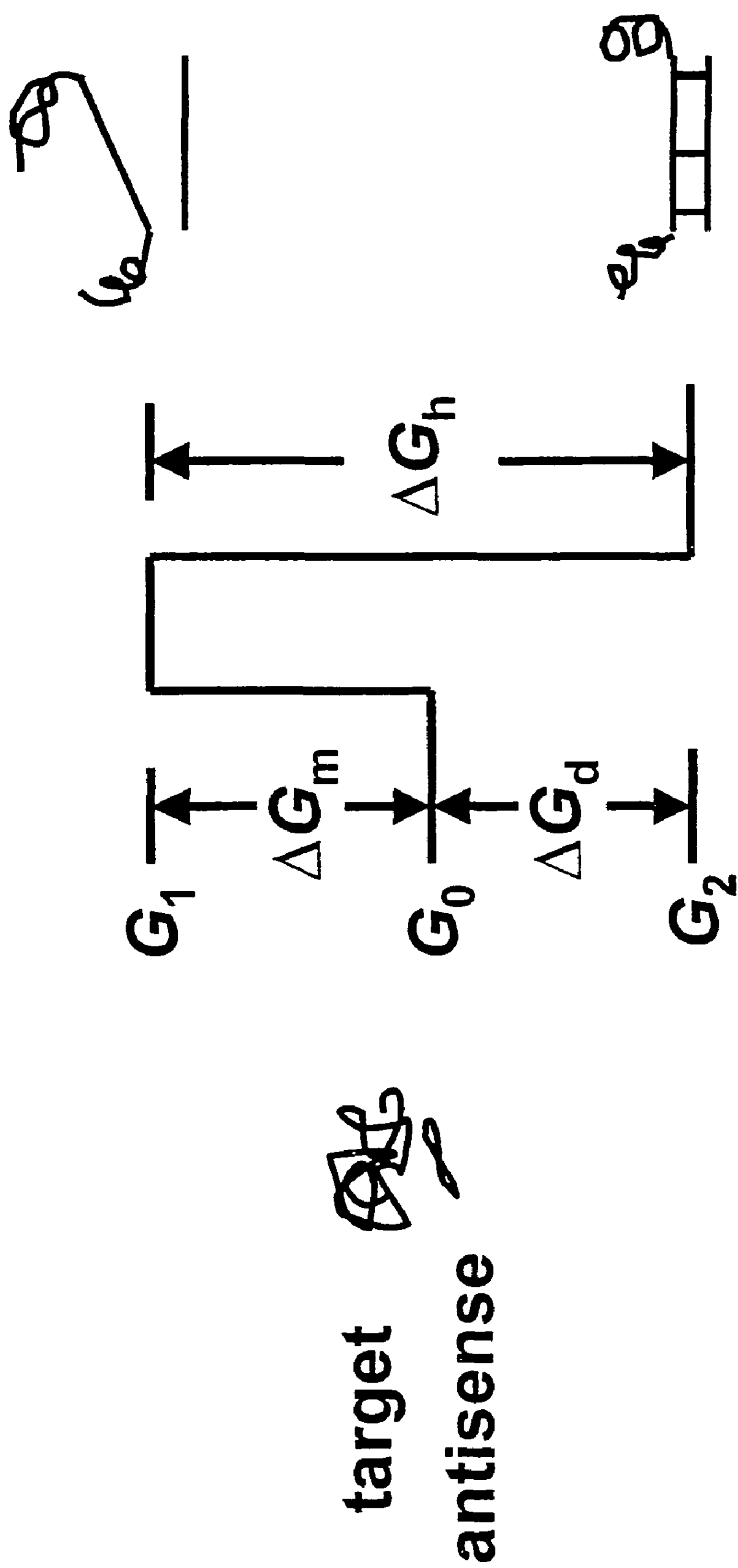
FIG. 1 illustrates energy changes associated with hybridization between antisense RNA and target RNA.

According to our invention, the activated state is considered to be an intermediate in which structures within the region that will hybridize are melted (FIG. 1). We have identified three parameters relevant to the kinetics of hybridization: (1) the melting energy, $\Delta G_m$ (the energy increase required to melt the structures in the target site and in the oligonucleotide), (2) the hybridization energy, $\Delta G_h$ (the energy decrease upon formation of a hybrid between the antisense oligonucleotide and the melted target site), and (3) the energy difference or energy advantage, $\Delta G_d$, between the final and the initial states. From these considerations we derived an expression that relates the target disappearance rate constant at steady state to the melting energy and the energy difference.

Our derivation begins with the rate of hybrid concentration change for reactions described by reaction 1. By considering the incoming flow, $k_1[A][S]$, and outgoing flow, $k_{-1}[AS]$ and $k_2[AS]$, we have $$d[AS]/dt=k_1[A][S]-k_{-1}[AS]-k_2[AS] \quad (2)$$

To obtain an explicit expression for the rate of target disappearance relevant to intracellular (steady-state) conditions, we utilize Briggs and Haldane's kinetic approach for the description of quasi steady-state conditions (Stryer, 1990). Accordingly, the hybrid concentration, [AS], is constant, or d[AS]/dt=0. Consequently, we have $$[AS] = \frac{k_1}{k_{-1}+k_2}[A][S] \quad (3)$$

The rate of product formation, which is also the target disappearance rate, is described by $$dP/dt = k_2[AS] = \frac{k_2 k_1}{k_{-1}+k_2}[A][S] = k_2[A][S]/K_m, \quad (4)$$

in which $K_m$ is $$K_m = \frac{k_{-1}+k_2}{k_1} \quad (5)$$

Thus for a steady-state reaction, the second-order association constant is $$k=k_2/K_m \quad (6)$$

For a single-tube assay, total antisense is conserved, and we have $[A_0]=[A]+[AS]$. The reaction rate can rewritten as $$dP/dt = k_2[AS] = \frac{k_2[A_0][S]}{K_m+[S]} \quad (7)$$

The second order association constant is $$k = \frac{k_2}{K_m+[S]} \quad (8)$$

To compare relative reaction rates for different sites in RNA, we assume that $k_2$ is approximately constant. Since $k_{-1}/k_1$ is the equilibrium constant for hybrid dissociation, therefore $$k_{-1}/k_1=e^{\Delta G_d/RT}. \quad (9)$$

For long targets, $k_1$ is determined by the melting energy barrier that impedes hybridization. From the Boltzmann distribution, the occupancy of the activated state is proportional to $e^{-\Delta G_m/RT}$. Following Pauling (Pauling, 1988), $$k_1=k_1^* e^{-\Delta G_m/RT} \quad (10)$$

where $k_1^*$ is the forward rate constant for the binding of the activated (melted) antisense oligonucleotide to the activated (melted) target site. $k_1^*$ is independent of RNA structure (the effect of structure is described by $e^{-\Delta G_m/RT}$ in Equation 10), but it is related to assay conditions, including cation concentration and temperature. Combining Equations 5, 9, and 10 leads to an expression for $K_m$:

$$K_m=Ce^{\Delta G_m/RT}+e^{\Delta G_d/RT}, \quad (11)$$

where C is a proportionality constant in which $$C=k_2/k_1^*. \quad (12)$$

Equations 6 and 8 are used to compare different sites in an RNA for antisense oligodeoxynucleotide attack. For this, we define an rate factor, $x=k/k_2$, or $$x = \frac{1}{Ce^{\Delta G m/RT} + e^{\Delta G d/RT}} \quad (13)$$

for steady-state reactions, and $$x = \frac{1}{(Ce^{\Delta G m/RT} + e^{\Delta G d/RT}) + [S]} \quad (14)$$

for single-tube assays. x reflects the relative rate at which a specified site hybridizes with an antisense nucleotide. Equation 13 is useful for comparing intracellular relative hybridization rate, and Equation 14 is useful for estimation of initial hybridization rate in a single-tube assay.

The terms $\Delta G_m$ and $\Delta G_d$ can be readily determined from commercially available RNA folding programs (e.g., the GCG package, available from the University of Wisconsin) that analyze the energy changes associated with the formation of RNA secondary structures, as described below. The melting energy, $\Delta G_m$, can be estimated using the lowest free energy to determine the difference between target RNA folded without restriction (the pre-hybridization state, $G_0$ in FIG. 1) and target RNA folded with the region of hybridizing nucleotides restricted to a single-stranded condition (activated state, $G_1$ in FIG. 1). The values of $k_2$ and C are assumed to be similar for different sites in an RNA when assayed by the same method under the same conditions. C can be determined from the experimental data as explained below.

Since magnesium ion concentration ($[Mg^{2+}]$), which is not considered in the calculation of energy parameters, can have profound effects on RNA tertiary structure (Pan and Sosnick, 1997) (Cate et al., 1997), we performed experiments at 0.2 and 10 mM $Mg^{2+}$. Changing the $[Mg^{2+}]$ in the reaction mixture in the 0.2-10 mM range had little effect on relative cleavage (data not shown). If tertiary interactions do occur in the target RNA, they are likely to have been present at 10 mM.$Mg^{2+}$ (Pan and Sosnick, 1997). Thus favorable sites in HIV-1 integrase RNA, as determined by the oligonucleotide-RNase H test, are not significantly affected by RNA tertiary structures, if they are present.

The method of this invention differs conceptually from previous work (Christoffersen et al., 1994; Mathews et al., 1999a; Patzel et al., 1999; Stull et al., 1992) because we used both $\Delta G_m$ and $\Delta G_d$, rather than only one of these parameters, for predicting hybridization rate. Our data support the logic (FIG. 1) of using both parameters. For the 17 favorable sites of HIV-1 integrase mRNA shown in FIG. 7A, moderate values for both $\Delta G_m$ and $\Delta G_d$ were calculated in 9 cases, very low values for $\Delta G_m$ were calculated in 5 cases, and very high values for $\Delta G_d$ were calculated in 3 cases. Thus both energy parameters play an important role in determining hybridization rate. As a comparison, poor correlation of percentage cleavage with overall energy change as calculated by the equilibrium method of Mathews et al is shown in the FIG. 7B.

Since dynamic processes are more likely to be relevant than equilibrium processes for use of oligonucleotides to inhibit gene expression, the steady-state model is more suitable for target site selection. The data presented show that most of the sites having high rate factors also exhibit rapid hybridization: when the rate factor is greater than $10^4$, then all the sites identified in c-myb mRNA (data not shown) and HIV-1 integrase (int) mRNA (FIG. 7) show cleavage levels that are at least half the maximal level. Thus our computational model generates few false positives (hybridization predicted to be rapid but is experimentally slow).

Equation 13 can be used to predict the rate of hybridization inside living cells. Since other work indicates that in vitro hybridization often translates into in vivo inhibitory effect (Jarvis et al., 1996; Lieber and Strauss, 1995; Lima et al., 1997; Matveeva et al., 1998), it is likely that the rate factor will be useful for identifying intracellular target sites for attack by oligodeoxynucleotides.

Since tertiary structure appears to be an insignificant factor in ODN-mRNA hybridization (the relative ability of sites to hybridize was insensitive to $[Mg^{2+}]$), the primary hurdle remaining in a priori identification of favorable sites may be the occlusion of intracellular sites by proteins bound to target RNA. Since some ribozymes and antisense nucleotides are effective inside cells and whole organisms, protein binding must not pose an insurmountable obstacle. Experiments with HIV-1 tat mRNA, expressed in a human cell line, show that the intracellular hybridizability of 16 sites to antisense attack correlate well with calculated rate factor (r=0.82). We conclude that use of the rate factor to identify target sites for antisense oligonucleotide hybridization can limit the number of sites that must be tested experimentally to just a few.

To test the kinetic model we calculated rate factors for hybridization of an artificial RNA fragment to six oligodeoxynucleotides (ODNs) and HIV-1 tat mRNA to molecular beacons. We then compared these values to initial hybridization rates that had been measured previously by another laboratory (Schwille et al., 1996) and by us. A good correlation was obtained. We also used the model to identify nucleation sites for RNA-RNA annealing that were in agreement with published experimental data. As a third test, we calculated rate factors for hybridization of ODNs to a wide range of sites in HIV-1 integrase mRNA (935 nt) and determined ODN-mediated RNase H cleavage of target RNA as a measure of accessibility. Predictions made using the method of this invention fit the experimental data with few exceptions. Additional retrospective examination of published data showed that our steady-state model has general applicability. Since target sites that are more favorable in in vitro hybridization are often more effective for antisense inhibition of gene expression in vivo (Matveeva et al., 1998), the method of this invention can be applied to mRNA in living cells. This expectation is supported by the results of the experiments described in Examples 5 to 6, in which antisense inhibition of the HIV-1 tat gene was examined using cultured human cells.

Figure 2:
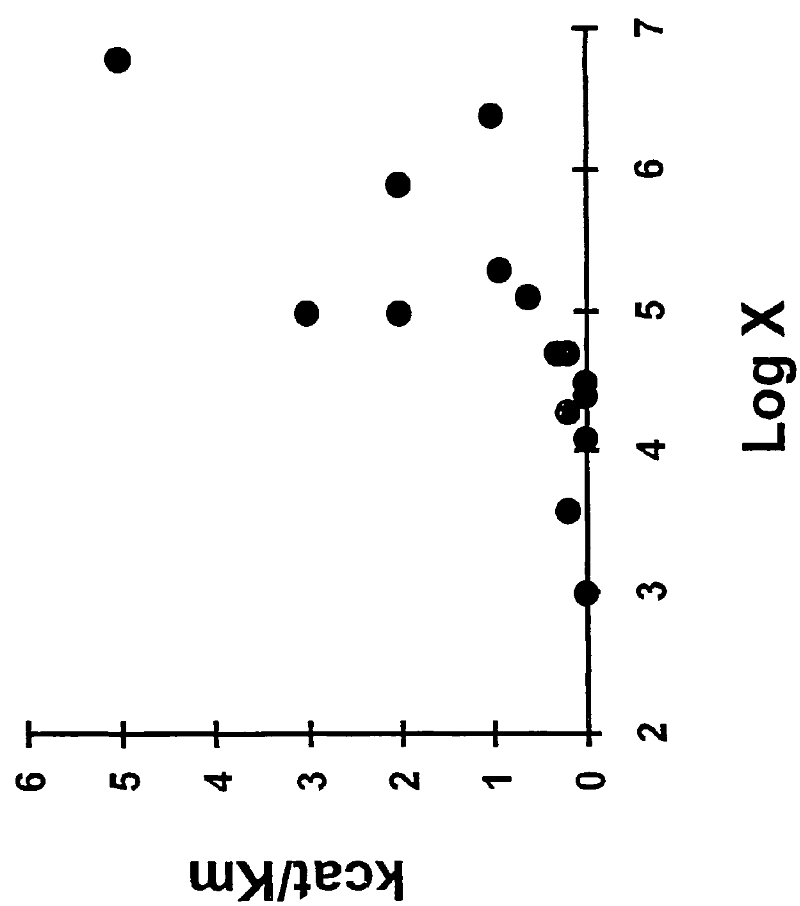
FIG. 2 is a plot of the relationship of calculated hybridization rate factor (x) with RNA product cleavage efficiency mediated by hammerhead ribozymes directed at HIV-1 vif-vpr gene.

As shown in FIG. 2, the rate factor $$x = \frac{1}{Ce^{\Delta G_m/RT} + e^{\Delta G_d/RT}} \quad \text{(Equation 13)}$$

for 15 hammerhead ribozymes targeted at HIV-1 vif-vpr RNA was calculated, for which $k_{cat}/K_m$ had been measured (Campbell et al., 1997 and personal communication with Campbell). The value of $k_{cat}/K_m$ was plotted versus calculated rate factor.

Calculation of Melting Energy ($\Delta G_m$) and Energy Difference ($\Delta G_d$)

Before hybridization can occur, the target and antisense nucleic acid (energy=$G_0$) must become single stranded in the region of the interaction (energy=$G_1$; see FIG. 1). The free energy required for melting the structure of the hybridization region is called the melting energy ($\Delta G_m = G_1 - G_0$). Hybridization results in a lower energy state (energy=$G_2$). The free energy difference between the hybridized state and the activated state ($G_2 - G_1$) is represented by $\Delta G_h$. The free energy difference between the state after hybridization and the state prior to hybridization ($G_2 - G_0$) is represented by $\Delta G_d$. In a typical case, $\Delta G_m$ is positive and $\Delta G_h$, and $\Delta G_d$ are negative.

To determine the rate factor, x, for a given target site, the melting energy needed to form the hybrid and the energy gained upon formation of the hybrid were calculated from the free energy of the initial, the activated, and the final (hybridized) states (see FIG. 1). The initial free energies of the antisense and the target RNA ($G_{0anti}$ and $G_{0target}$) were obtained from the output files of the GCG RNA folding program FoldRNA (GCG Package Version 9.1-Unix, Genetics Computer Group, University of Wisconsin, Madison). The free energies for the activated antisense oligonucleotide ($G_{1anti}$) and the activated target RNA ($G_{1target}$) were obtained in the same way, but with the hybridization regions constrained in a single-stranded conformation, using the online command PREVENT. For large RNA targets, only the 500 nucleotides within which the site is embedded were included in the folding. Since these folding programs can analyze only one molecule at a time, the free energy of hybridization, $\Delta G_h$, was calculated using a program that we wrote in the C programming language. This program, which uses thermodynamic parameters measured by others (Mathews et al., 1999b; SantaLucia, 1998), is available upon request from Jian-Ying Wang, Public Health Research Institute, New York.

The energy of the final state, $G_2$, the melting energy, $\Delta G_m$, and the energy difference $\Delta G_d$ were calculated as follows:

$$G_2=(G_{1anti}+G_{1target})+\Delta G_h, \tag{15}$$

$$\Delta G_m=(G_{1anti}+G_{1target})-(G_{0anti}+G_{0target}), \tag{16}$$

$$\Delta G_d=G_2-(G_{0anti}+G_{0target}). \tag{17}$$

The values of $\Delta G_m$ and $\Delta G_d$ were then substituted into Equations 7-15. Using the data for HIV-1 integrase mRNA, we found that $C=10^{-8}$ for in vitro hybridization and and $C=10^{-11}$ for intracellular activity gave the least scatter. Consequently we used these empirically determined numbers for all calculations involving antisense DNA oligonucleotides. To consider many sites, we utilized a script program written in UNIX (see below) to carry out recurring calculations. Curve fitting was accomplished using the program DeltaGraph (DeltaPoint, Inc.).

UNIX Scripts

Examples of suitable computer programs follow. While the programs are scripted for a UNIX-based system, it will be apparent that programs for other platforms and/or programs written in other programming languages can be substituted for the following:

A script for
UNIX to search accessible sites for antisense ODN attack of RNA

```
#!/bin/csh
# Filename: fldasscan.
# Command syntax: csh fldasscan target lhyb step Star Etar Sas Eas
1/2window
# lhyb is the length of hybridization region.
# Star,Etar is the start and end of target RNA in sequence of target.
# Sas,Eas is the start and end of antisense RNA in sequence of antisense.
# 1/2window is half of window in target in which folding energy
considered.
# Before start, copy target and antisense sequences into the directory.
#
#The GCG package must be initiated
#GCGQID must be undefined to start a logical name server
#
unsetenv GCGQID
    gcg10
    gcg
    Laser11
set prof = $1;set ln = $2;set step = $3;set Star = $4; set Etar = $5
set Santi = $6; set Eanti = $7; set halfwindow = $8
@S_E = $Star – $Etar
cat > $prof.fldasscan << EOF
The command your issured is "csh fldasscan $prof $ln $step $Star $Etar
$Santi
$Eanti $halfwindow"
Target RNA from $Star to $Etar, AntiHybRegion $Santi – $Eanti,
AntiLength = $ln
Energy window = 2 X $halfwindow
EOF
date > $prof.fldasscan
@a = $Santi; @b = ($a + $ln) – 1
while ($b <= $Eanti)
echo "$a" "$b"
@a_S = $a – $Star; @b_E = $Etar – $b
```

-continued

```
if ($a_S <= $halfwindow) then
        set s = $Star
echo "$s"
else
        @s = $a – $halfwindow
endif
echo "$s"
@e = ($s + $ln) + (2 * $halfwindow)
if($b_E <= $halfwindow) then
        @ e = $Etar; @s = ($Etar – $ln) – (2 * $halfwindow)
endif
echo "$s" "$e"
reverse -inf=$prof -outf=anti -begin=$a -end=$b -defau
assemble -inf=$prof -outf=subseq -begin=$a -end=$b -default
assemble -inf=@cshinfsla -outf=sub_anti$a -default
foldrna -INfile=$prof -begin=$s -end=$e -Default
foldrna -INfile=$prof -outf1=$prot$a.fld -outf2=$prof$a.connect\
-begin=$s -end=$e -prev=$a,0,$ln -Default
foldrna -inf=sub_anti$a -Default
# cshrna_dna is a program in C that is listed at the end of this section.
cshrna_dna
cat >> $prof.fldasscan << EOF
        Hybridization site $a – $b (window $s – $e)
Flanking length $a – $b_$ln
EOF
    grep Energy $prof.connect >> $prof.fldasscan
    grep Energy $prof$a.connect >> $prof.fldasscan
    grep Energy sub_anti$a.connect >> $prof.fldasscan
    grep Energy sub.connect >> $prof.fldasscan
# cshrna_rna is a program in C that is listed at the end of this section.
cshrna_rna
    grep Energy sub.connect >> $prof.fldasscan
rm *.fld; rm *.connect; rm su*
@a = $a + $step; @b = ($a + $ln) – 1
end
#sub-program "cshrna_dna"
#include <stdio.h>
#include <stdlib.h>
#include <ctype.h>
#include <string.h>
int main(void)
{
            char sub[54], line[54],*pattern;
            double Energy = 3.1;
            int i,n = 15, s0, s1;
            FILE *ifp, *ofp;
            ifb = fopen("subseq", "r");
            ofp = fopen("sub.connect", "w");
            pattern = "   1 ";
    while(fgets(line, 50, ifp) != NULL){
        if(strstr(line, pattern) != NULL){
            printf("\n%s has been found befor\n", pattern);
            strcpy(sub, line + 10);
            printf("%s\n", sub);
        }
    }
    for(i = 0; i < 40; ++i){
        if(sub[i] != ''){
            if(sub[i + 1] !='' && sub[i + 1] !='\0'){
            s0 = tolower(sub[i]); s1 = tolower(sub [i + 1]);
            }
            else if(sub[i + 1] == ''){
            s0 = tolower(sub[i]); s1 = tolower(sub[i + 2]);
            }
            else if(sub[i + 1] == '\0')}
                s0 = ''; s1 = '';
                printf("The end --- %dth round\n", i);
            }
        }
        else{
            s0 = ''; s1 = '';
        }
```

-continued

```
        printf("%c%c\n", s0, s1);
        switch(s0){
            case 'a':
                switch(s1){
                    case 'a': Energy = Energy - 1.0; break;
                    case 'c': Energy = Energy - 2.1; break;
                    case 'g': Energy = Energy - 1.8; break;
                    case 't': Energy = Energy - 0.9; break;
                }
                break;
            case 'c':
                switch(s1){
                    case 'a': Energy = Energy - 0.9; break;
                    case 'c': Energy = Energy - 2.1; break;
                    case 'g': Energy = Energy - 1.7; break;
                    case 't': Energy = Energy - 0.9; break;
                }
                break;
            case 'g':
                switch(s1){
                    case 'a': Energy = Energy - 1.3; break;
                    case 'c': Energy = Energy - 2.7; break;
                    case 'g': Energy = Energy - 2.9; break;
                    case 't': Energy = Energy - 1.1; break;
                }
                break;
            case 't':
                switch(s1){
                    case 'a': Energy = Energy - 0.6; break;
                    case 'c': Energy = Energy - 1.5; break;
                    case 'g': Energy = Energy - 1.6; break;
                    case 't': Energy = Energy - 0.2; break;
                }
                break;
            }
            printf("%f \n", Energy);
    }
        fclose(ifp);
        printf("\nTotal Energy: %f\n", Energy);
        fprintf(ofp, "Flanking length \n");
        fprintf(ofp, "Length__ Energy: %6.1f\n", Energy);
        fclose(ofp);
        return 0;
}
# cshrna__rna:
#include <stdio.h>
#include <stdlib.h>
#include <ctype.h>
#include <string.h>
int main(void)
{
            char sub[54], line[54],*pattern;
            double Energy = 3.4;
            int i,n = 15, s0, s1;
            FILE *ifp, *ofp;
            ifp = fopen("subseq", "r");
            ofp = fopen("sub.connect", "w");
            pattern = "   1 ";
while(fgets(line, 50, ifp) != NULL){
    if(strstr(line, pattern) != NULL){
        printf("\n%s has been found befor\n", pattern);
        strcpy(sub, line + 10);
        printf("%s\n", sub);
    }
}
for(i = 0; i < 40; ++i){
if(sub[i] != ''){
    if( sub[i + 1] != '' && sub[i + 1] != '\0'){
    s0 = tolower(sub[i]); s1 = tolower(sub [i + 1]);
    }
    else if(sub[i + 1] == ''){
        s0 tolower(sub[i]); s1 = tolower(sub[i + 2]);
        }
        else if(sub[i + 1] == '\0'){
        s0 = ''; s1 = '';
        printf("The end --- %dth round\n", i);
    }
}
else{
        s0 = ''; s1 = '';
}
printf("%c%c\n", s0, s1);
        switch(s0){
            case 'a':
                switch(s1){
                    case 'a': Energy = Energy - 0.9; break;
                    case 'c': Energy = Energy - 2.1; break;
                    case 'g': Energy = Energy - 1.7; break;
                    case 't': Energy = Energy - 0.9; break;
                }
                break;
            case 'c':
                switch(s1){
                    case 'a': Energy = Energy - 1.8; break;
                    case 'c': Energy = Energy - 2.9; break;
                    case 'g': Energy = Energy - 2.0; break;
                    case 't': Energy = Energy - 1.7; break;
                }
                break;
            case 'g':
                switch(s1){
                    case 'a': Energy = Energy - 2.3; break;
                    case 'c': Energy = Energy - 3.4; break;
                    case 'g': Energy = Energy - 2.9; break;
                    case 't': Energy = Energy - 2.1; break;
                }
                break;
            case 't':
            switch(s1){
                    case 'a': Energy = Energy - 1.1; break;
                    case 'c': Energy = Energy - 2.3; break;
                    case 'g': Energy = Energy - 1.8; break;
                    case 't': Energy = Energy - 0.9; break;
                }
                break;
            }
            printf("%f\n", Energy);
}
        fclose(ifp);
        printf("\nTotal Energy: %f\n", Energy);
        fprintf(ofp, "Flanking length \n");
        fprintf(ofp, "Length__ Energy: %6.1f\n", Energy);
        fclose(ofp);
        return 0;
}
# cshinfsla is a file list:
            subseq
            cshlinker
            anti
```

A script for UNIX to search for nucleation site of RNA-RNA annealing

```
#!/bin/csh
# Filename: fldasrna.
# Command syntax: csh fldasrna target as lhyb step Star Etar Sas Eas
#A0 B0 a0 b0 S1as.
# A0 and B0: boundaries of hyb. region in target;
# a0 an b0: boundaries of hyb region in antisense.
# lhyb is the length of hybridization region.
# Star,Etar is the start and end of target RNA in sequence of target.
# Sas,Eas is the start and end of antisense RNA in sequence of
# antisense.
# S1as is the first nt of 5' truncated antisense.
# Before start, copy target and antisense sequences into the directory
#The GCG package must be initiated
#GCGQID must be undefined to start a logical name server #
unsetenv GCGQID
gcg10
gcg
Laser11
set target = $1; set as = $2
set lhyb = $3; set step = $4; set Star = $5; set Etar = $6
set Sas = $7;set Eas = $8; set A0 = $9; set B0 = $10
set a0 = $11; set b0 = $12; set S1as = $13; set S2as = $14
cp $target target
cp $as as
cat > $target.fldasrna <<EOF
Command you issued is "csh fldasrna $target $as $lhyb $step $Star
```

-continued

```
$Etar $Sas $Eas $A0 $B0 $a0 $b0 $S1as $S2as"
Today is
EOF
date >> $target.fldasrna
#5' truncated antisense when Sas <= a0
cat >> $target.fldasrna <<EOF
Antisense $Sas__$Eas (Sas <= a0)
EOF
@a = $a0; @b = ($a + $lhyb) − 1
@B = $B0; @A = ($B − $lhyb) + 1
while ($Sas <= $a0)
cat >> $target.fldasrna <<EOF
Truncated as: nt $Sas__$Eas
EOF
while ($b <= $b0)
foldrna as -begin=$Sas -end=$Eas -default
foldrna as -begin=$Sas -end=$Eas -prev=$a,0,$lhyb \
-outf1=as.$a.fld -outf2=as.$a.connect -defaul
reverse as -begin=$a -end=$b -outf=subseq -default
# cshrna__rna is a sub-program written in C.
cshrna__rna
# Folding target
foldrna target -begin=$Star -end=$Etar -default
foldrna target -begin=$Star -end=$Etar -prev=A,0,$lhyb \
-outf1=tar.$A.fld -outf2=tar.$A.connect -default
cat >> $target.fldasrna <<EOF
Annealing Regions $A − $B__$a − $b
EOF
grep Energy target.connect >> $target.fldasrna
grep Energy tar.$A.connect >> $target.fldasrna
grep Energy as.connect >> $target.fldasrna
grep Energy as.$a.connect >> $target.fldasrna
grep Energy sub.connect >> $target.fldasrna
rm *fld; rm *.connect
@a = $a + $step; @b = ($a + $lhyb) − 1
@B = $B − $step; @A = ($B − $lhyb) + 1
end
@Sas = $Sas + $step
@a = $a0; @b = ($a + $lhyb) − 1
@B = $B0; @A = ($B − $lhyb) + 1
end
# WhenSas > a0.
@Sas = $a0 + $step
@a = $Sas; @b = ($a + $lhyb) − 1
@B = $B0 − $step; @A = ($B − $lhyb) + 1
set a0 = $Sas; set B0 = $B
while ($Sas <= $S1as)
cat >> $target.fldasrna <<EOF
Antisense $Sas__$Eas (Sas > a0)
EOF
cat >> $target.fldasrna <<EOF
Truncated as: nt $Sas__$Eas
EOF
while ($b <= $b0)
foldrna as -begin=$Sas -end=$Eas -default
foldrna as -begin=$Sas -end=$Eas -prev=$a,0,$lhyb \
-outf1=as.$a.fld -outf2=as.$a.connect -defaul
reverse as -begin=$a -end=$b -outf=subseq -default
# cshrna__rna is a sub-program written in C, which will be provided
# upon request.
cshrna__rna
# Folding target
foldrna target -begin=$Star -end=$Etar -default
foldrna target -begin=$Star -end=$Etar -prev=$A,0,$lhyb \
-outf1=tar.$A.fld -outf2=tar.$A.connect -default
cat >> $target.fldasrna <<EOF
Annealing Regions $A − $B__$a − $b
EOF
grep Energy target.connect >> $target.fldasrna
grep Energy tar.$A.connect >> $target.fldasrna
grep Energy as.connect >> $target.fldasrna
grep Energy as.$a.connect >> $target.fldasrna
grep Energy sub.connect >> $target.fldasrna
rm *.fld; rm *.connect
@a = $a + $step; @b = ($a + $lhyb) − 1
@B = $B − $step; @A = ($B − $lhyb) + 1
end
@Sas = $a0 + $step
@a = $Sas; @b = ($a + $lhyb) − 1
```

-continued

```
@B = $B0 − $step; @A = ($B − $lhyb) + 1
set a0 = $Sas; set B0 = $B
end
#3' truncated antisense when Eas >= b0
set Sas = $7;set Eas = $8; set A0 = $9; set B0 = $10
set a0 = $11; set b0 = $12
cat >> $target.fldasrna <<EOF
Antisense $Sas__$Eas (Eas >= b0)
EOF
@a = $a0; @b = ($a + $lhyb) − 1
@B = $B0; @A = ($B − $lhyb) + 1
while ($Eas >= $b0)
cat >> $target.fldasrna <<EOF
Truncated as: nt $Sas__$Eas
EOF
while ($b <= $b0)
foldrna as -begin=$Sas -end=$Eas -default
foldrna as -begin=$Sas -end=$Eas -prev=$a,0,$lhyb \
-outf1=:as.$a.fld -outf2=as.$a.connect -defaul
reverse as -begin=$a -end=$b -outf=subseq -default
# cshrna__rna is a sub-program written in C.
cshrna__rna
# Folding target
foldrna target -begin=$Star -end=$Etar -default
foldrna target -begin=$Star -end=$Etar -prev=$A,0,$lhyb \
-outf1=tar.$A.fld -outf2=tar.$A.connect -default
cat >> $target.fldasrna <<EOF
Annealing Regions $A − $B__$a − $b
EOF
grep Energy target.connect >> $target.fldasrna
grep Energy tar.$A.connect >> $target.fldasrna
grep Energy as.connect >> $target.fldasrna
grep Energy as.$a.connect >> $target.fldasrna
grep Energy sub.connect >> $target.fldasrna
rm *fld; rm *.connect
@a = $a + $step; @b = ($a + $lhyb) − 1
@B = $B − $step; @A = ($B − $lhyb) + 1
end
@Eas = $Eas − $step
@a = $a0; @b = ($a + $lhyb) − 1
@B = $B0; @A = ($B − $lhyb) + 1
end
# When Eas<b0.
@Eas = $b0 − $step
@a = $a0; @b = ($a + lhyb) − 1
@B = $B0; @A = ($B − $lhyb) + 1
set b0 = $Eas
while ($Eas >= $S2as)
cat >> $target.fldasrna <<EOF
Antisense $Sas__$Eas (Eas<b0)
EOF
cat >> $target.fldasrna <<EOF
Truncated as: nt $Sas__$Eas
EOF
while ($b <= $b0)
foldrna as -begin=$Sas -end=$Eas -default
foldrna as -begin=$Sas -end=$Eas -prev=$a,0,$lhyb \
-outf1=as.$a.fld -outf2=:as.$a.connect -defaul
reverse as -begin=$a -end=$b -outf=subseq -default
# cshrna__rna is a sub-program written in C, which will be provided
# upon request.
cshrna__rna
# Folding target
foldrna target -begin=$Star -end=$Etar -default
foldrna target -begin=$Star -end=$Etar -prev=$A,0,$lhyb \
-outf1=tar.$A.fld -outf2=tar.$A.connect -default
cat >> $target.fldasrna <<EOF
Annealing Regions $A − $B__$a − $b
EOF
grep Energy target.connect >> $target.fldasrna
grep Energy tar.$A.connect >> $target.fldasrna
grep Energy as.connect >> $target.fldasrna
grep Energy as.$a.connect >> $target.fldasrna
grep Energy sub.connect >> $target.fldasrna
rm *.fld; rm *.connect
@a = $a + $step; @b = ($a + $lhyb) − 1
@B = $B − $step; @A = ($B − $lhyb) + 1
end
@Eas = $b0 − $step
```

-continued

```
@a = $a0; @b = ($a + $lhyb) − 1
@B = $B0; @A = ($B − $lhyb) + 1
set b0 = $Eas
end
```

Measurement of Hybridization

Radioactively labeled target mRNA was obtained by in vitro transcription from the HIV-1 int gene using bacteriophage T7 RNA polymerase and the expression plasmid pLJS10 (Sioud and Drlica, 1991). Target site hybridizability was measured by hybridization of antisense DNA oligonucleotides to preselected sites in int RNA. Equimolar amounts of oligonucleotide and mRNA (~0.2 pmol) were incubated at 37° C. for the indicated times in the presence of 0.1 unit RNase H (GIBCO) in a 5-μl solution containing 20 mM Tris-HCl (pH 7.8), 100 mM KCl, and various concentrations of $MgCl_2$. The reactions were stopped by the addition of an equal volume of 10 mM Tris-HCl (pH.8.3), 10 mM EDTA, 0.1% bromophenol blue, 0.1% xylene cyanole, and 96% formamide. For each antisense oligonucleotide, the disappearance of intact target was assayed by 6% urea polyacrylamide gel electrophoresis and PhosphorImager scanning.

Antisense Activity in Cultured Human Cells

Using the method of this invention, a hybridization rate factor was calculated for 16 regions of mRNA from the tat gene of HIV-1, and a complementary antisense oligonucleotide for each site was constructed and tested for the ability to inhibit Tat expression in the human cell line 293. Calculated rate factor and intracellular antisense activity correlated well (r=0.8; p<0.001), as did hybridization of mRNA in vitro and inhibition of intracellular gene expression. Thus, we found that RNA tertiary structure and intracellular RNA-binding proteins, which are absent in vitro, had little effect on antisense ODN hybridization to mRNA in this system. We conclude that the computational model can be used to select mRNA target sites that are most suitable for hybridization, bypassing time-consuming trial-and-error experimentation.

Figure 12:
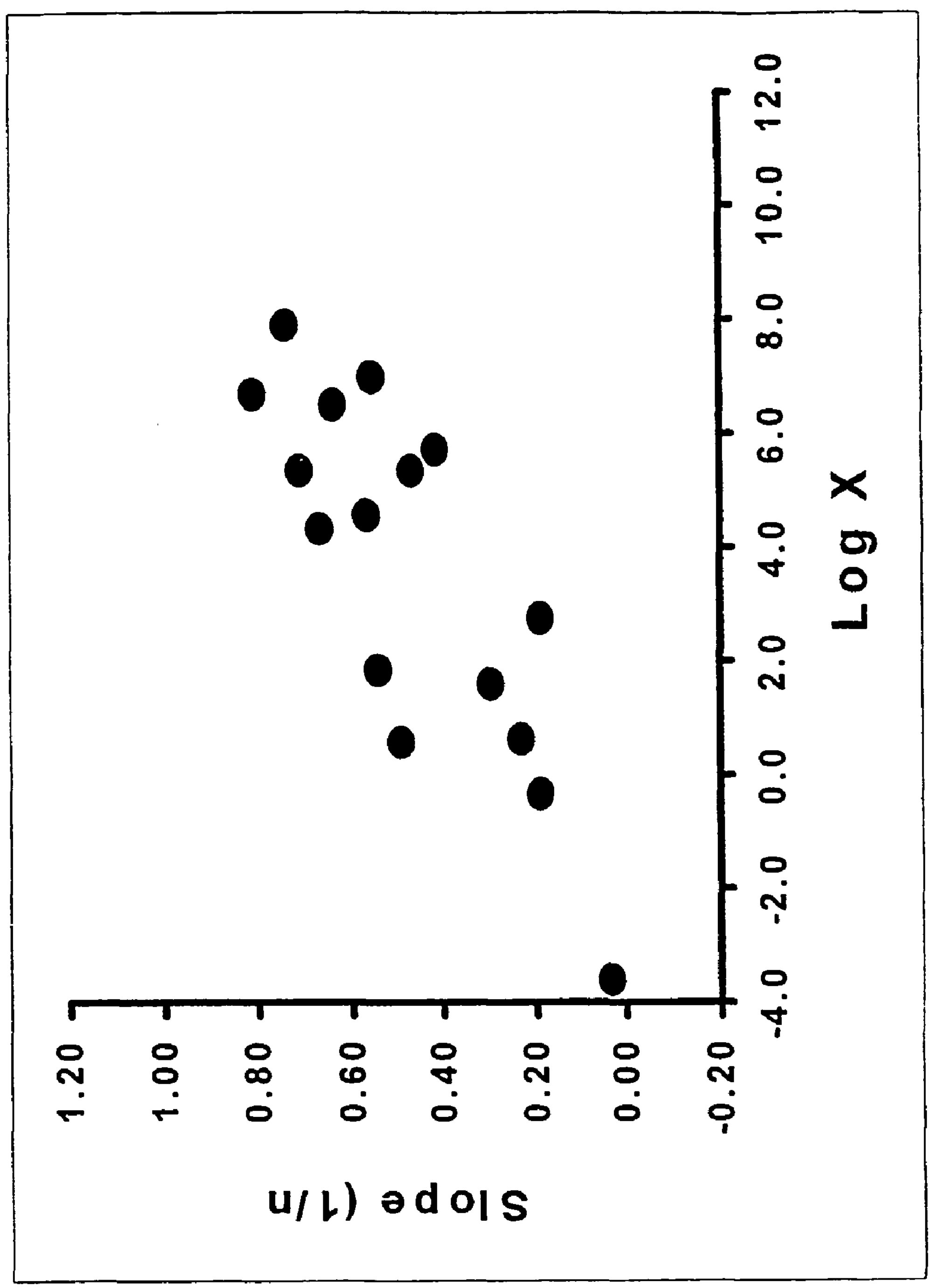
FIG. 12 illustrates the correlation between calculated hybridizability and intracellular inhibitory effect of ODNs as measured by fluorescence decrease.
Figure 13:
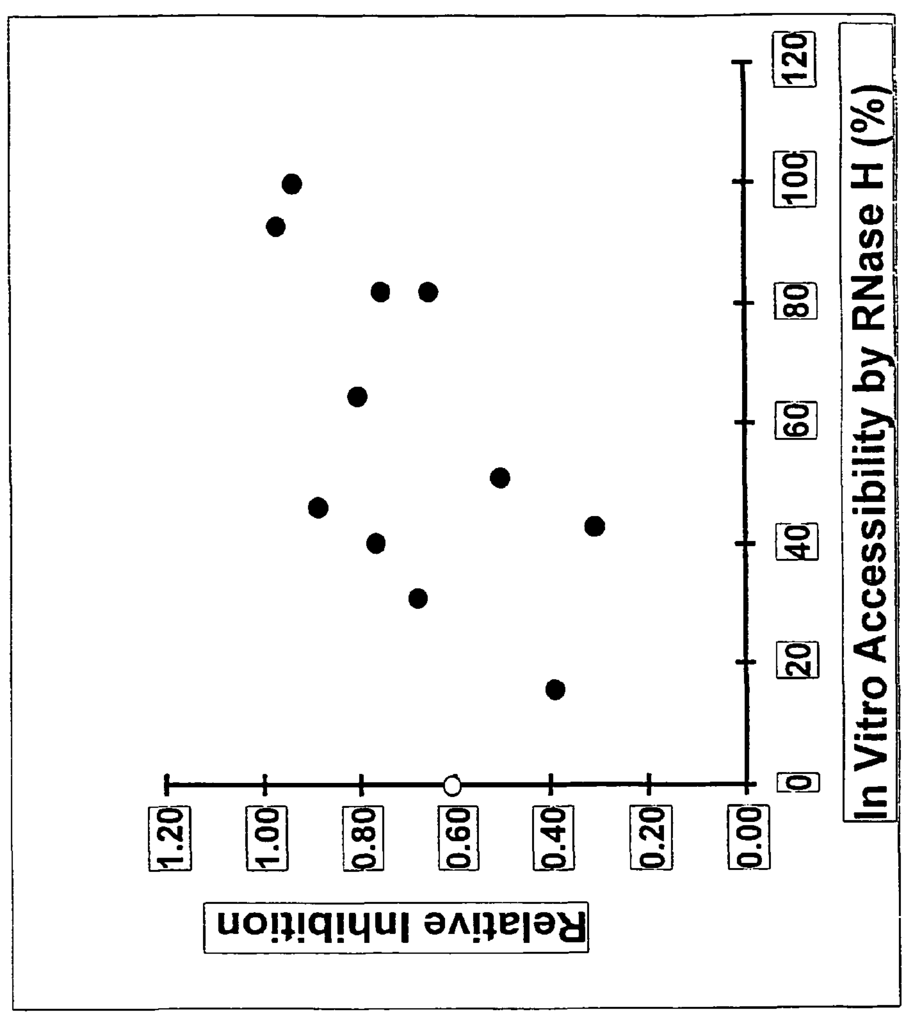
FIG. 13 shows the correlation between the efficiency of intracellular inhibition of HIV-1 tat expression and RNase H cleavage of tat RNA in vitro mediated by antisense ODNs.

The experiments described above show that the method of the invention for hybridization rate applies under intracellular conditions: the calculated rate factor for ODN-mRNA hybridization correlated with ODN antisense activity (FIG. 12). Cleavage products of tat mRNA due to RNase H action were resolved with 6% urea PAGE and were quantified with PhosphorImager. The percentage of cleavage mediated by each ODN was plotted versus the rate factor calculated using Equation 13. Most of the sites exhibit a high degree of correlation between intracellular activity and hybridization in vitro when assayed by RNase H-mediated RNA cleavage (FIG. 13). These results indicate that most of the sites in an intracellular mRNA are not occluded by proteins or other factors. Since the computational model ignores tertiary structure, such structure is not an important factor in the ability of antisense oligonucleotides to hybridize to mRNA. A practical implication of the present work is that favorable sites for antisense attack can be determined by calculation rather than by the labor- and time-consuming process of oligonucleotide library screening. Among the 16 ODNs tested in this work, several have been used for inhibition of HIV-1 replication (Hendry et al., 1997; Jackson et al., 1998; Sun et al., 1995; Zhou et al., 1994). The best, #8161, was identified by our model as being directed at a highly favorable site.

The invention is further described in the following examples, which do not limit the scope of the invention described in the claims.

EXAMPLES

Example 1

Correlation of Initial Rate Constant for Oligodeoxynucleotide-RNA Hybridization We first tested the ability of Equation 14 to predict initial hybridization rate using a 101-nucleotide RNA target for which initial hybridization rates of 5 antisense DNA oligonucleotides have been measured (Schwille et al., 1996). FIG. 3A (left) shows the secondary structures of the RNA target and antisense DNA as predicted by GCG FOLDRNA program.

The antisense DNAs with lengths ranging from 19 to 37 nucleotides are targeted at different sites. We assume that hybridization begins with nucleation in a sub-region of base pairing that has the maximum hybridization rate constant among all sub-regions of the molecule.

We calculated the values of $$x = \frac{1}{(Ce^{\Delta G}m/RT + e^{\Delta G}d/RT) + [S]}$$

for all the sub-regions having 15 nt for each antisense oligonucleotide where $[S_0]$ is the initial concentration of target RNA. The maximum, taken as $k/k_2$, was compared with measured initial binding constant in Table 1 and in FIG. 3B (right), which shows the correlation between calculated maximum value of x=

$$x = \frac{1}{(Ce^{\Delta G}m/RT + e^{\Delta G}d/RT) + [S]}$$

for sub-regions with 15 nt size and measured initiation binding rate of antisense DNA oligonucleotide complementary to various regions of the target RNA.

TABLE 1

Antisense oligodeoxynucleotides for which initial hybridization rate has been measured

| # | Pairing region | Measured init. rate | Calculated x |
|---|---|---|---|
| 1 | 1-19 | $3.77 \times 10^5$ | $2.4 \times 10^8$ |
| 2 | 9-37 | too low to measure | $1.1 \times 10^3$ |
| 3 | 26-62 | $2.13 \times 10^4$ | $5.4 \times 10^4$ |
| 4 | 40-70 | $2.46 \times 10^5$ | $9.0 \times 10^6$ |
| 5 | 65-81 | $1.35 \times 10^5$ | $1.9 \times 10^8$ |
| 6 | 79-101 | $9.15 \times 10^5$ | $1.1 \times 10^9$ |

We also calculated rate factors for hybridization of 4 molecular beacons to HIV-1 tat mRNA and measured the initial rate of hybridization. Molecular beacons are antisense molecules with a stem-loop structure in which the antisense sequence is in the loop region. To one end of a molecular beacon is attached a fluorophore that emits fluorescence upon UV irradiation. The other end is attached to a quencher that absorbs the fluorescence emitted by the fluorophore when the stem region is base-paired. When antisense sequences in the loop region hybridize to a complementary target, the fluorophore and the quencher separate, and fluorescence is observed after UV irradiation. Table 2 shows the correlation between rate factor and measured initial hybridization rate.

TABLE 2

Initial velocities and calculated rate factors of hybridization to tat mRNA for four molecular beacons

| Beacon # | Initial Velocity ($min^{-1}$) | Log x[a] |
|---|---|---|
| 264 | 43 | 3.1 |
| 267 | 22 | 1.7 |
| 282 | 2 | −0.3 |
| 226 | <0.1 | −0.9 |

[a]calculated using Equation 14.

Example 2

Identification of Nucleation Sites for RNA-RNA

RNA-RNA annealing is proposed to initiate through contacts over a short region (kissing) that lead to formation of a stable complex. The stable nucleation complex is then elongated to form full-length hybrid. Nucleation is expected to be rate limiting for long RNA-RNA hybridization; therefore considerable effort has been made to understand the elements required for nucleation. The loop-loop contact model asserts that rapid hybridization begins with contact between loops present in both antisense and target RNA. Although the model explains some examples, others exist in which the initial contact regions are not in loops. It has been difficult to predict nucleation regions from sequence information because loop regions must be determined by single-strand mapping and because multiple loops may be present. Equation 14 can be used to identify nucleation sites as regions having maximum hybridization rate factor when calculated stepwise for short base-pairing regions.

Figure 4A:
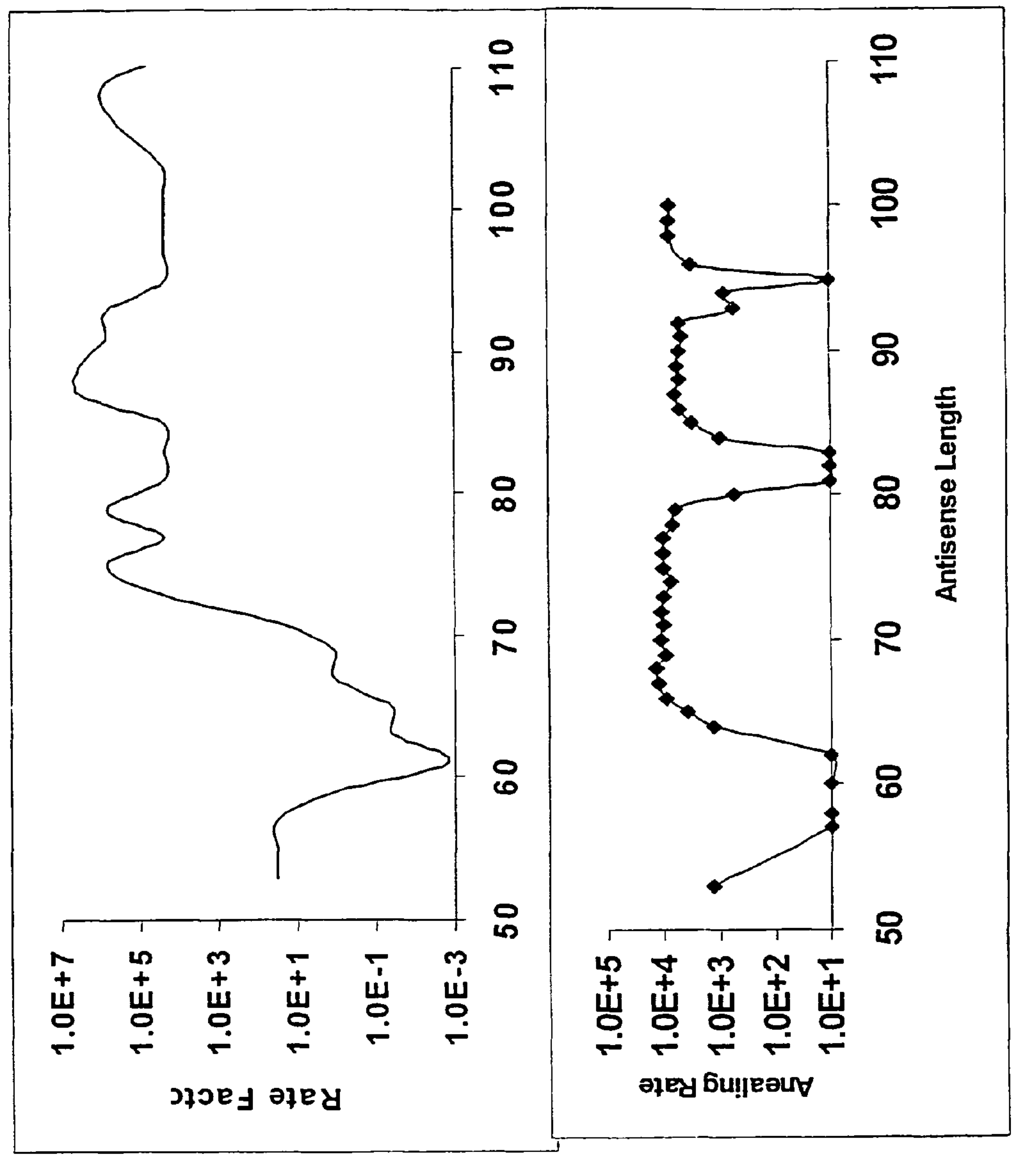
FIG. 4A is a set of graphs indicating hybridization rate factor (x) calculated for a series of antisense oligonucleotides hybridized to HIV-1 RNA (top); and experimental hybridization rate (bottom). The pattern reflects change in antisense structure as length is changed; calculated minima correlate with observed minima.
Figure 4B:
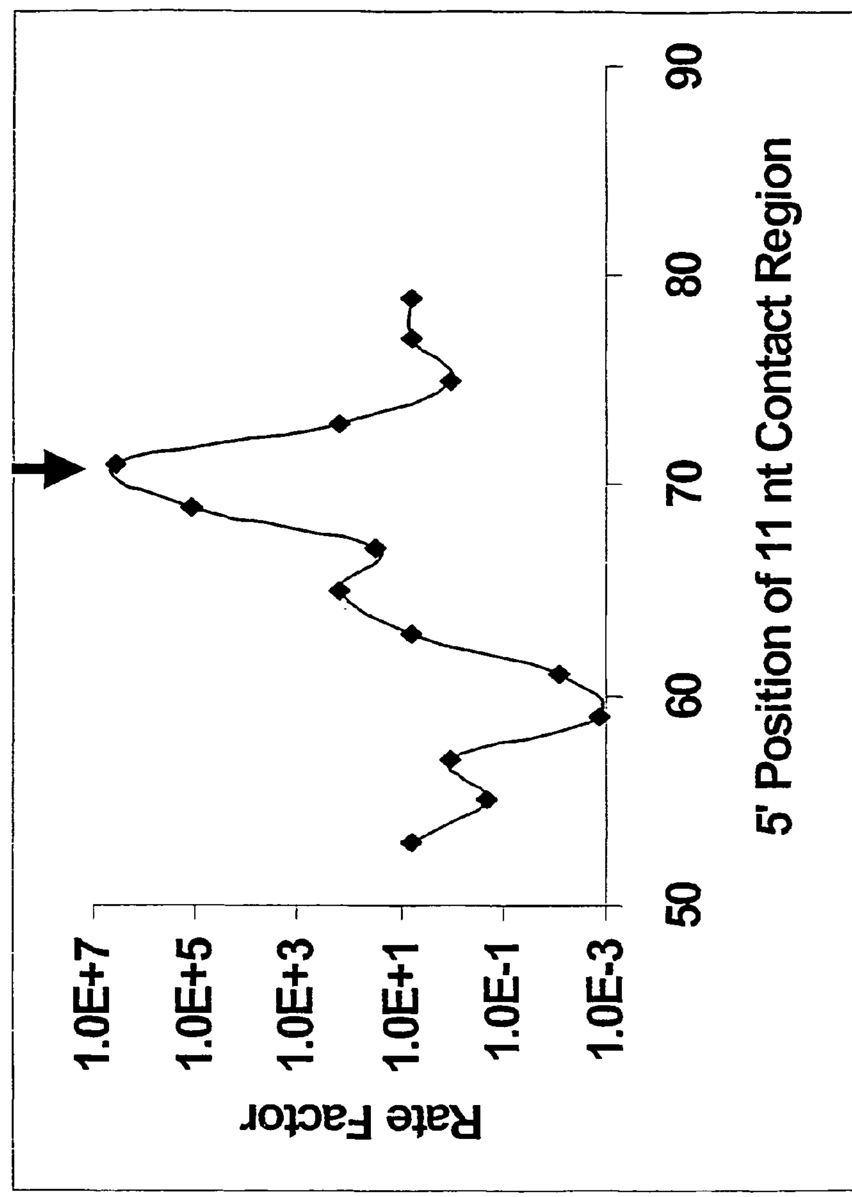
FIG. 4B is a graph showing the calculated hybridization rate factor (x) at various positions in the HIV-1 target RNA described in FIG. 4A. The arrow indicates the position of an experimentally determined nucleation site.

As one test of Equation 14 we examined hybridization data presented by the Sczakiel group (Rittner et al., 1993). In that work a series of anti-HIV-1 RNAs had been prepared in which all members of the set had a common 5' end but differed at the 3' end and therefore differed in length. When hybridized to HIV-1 RNA these molecules exhibited striking differences that depended on length (FIG. 4A, bottom). We used Equation 14 to calculate the rate factor (x) for 11 nucleotide-long regions at all possible positions for each antisense tested by the Sczakiel group (Rittner et al., 1993). When the maximum value of x was plotted for each antisense oligonucleotide (FIG. 4A, top), the data coincided with the data of Sczakiel (Rittner et al., 1993). Sczakiel et al (Homann et al., 1993) then explained the pattern shown in FIG. 4A (bottom) as being due to nucleation sites. They identified one such site by mutagenesis ((Homann et al., 1993); arrow, FIG. 4B). The location of that site corresponded to the location of the maximal value of rate factor calculated for each antisense (FIG. 4B). Thus, we are able to use Equation 14 to identify nucleation sites.

Figure 5A:
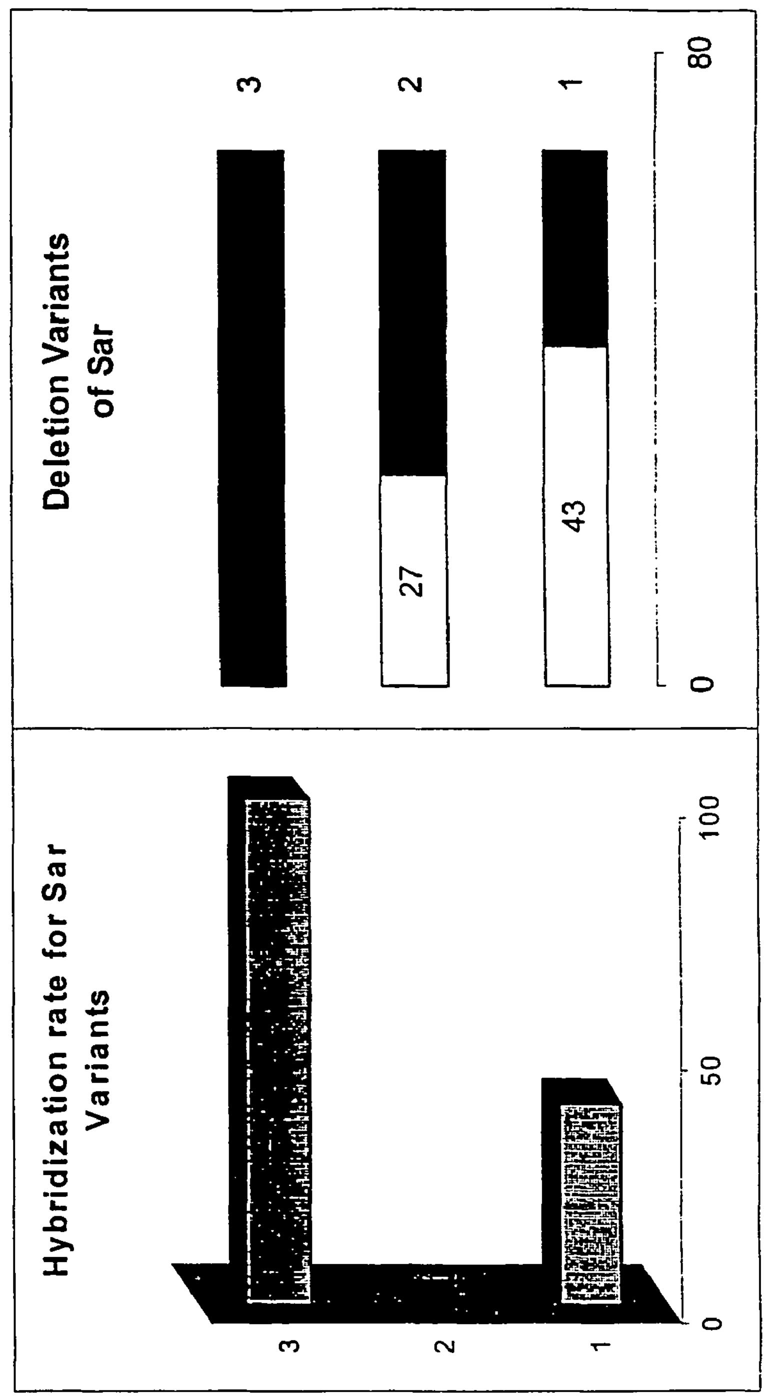
FIG. 5A is a set of graphs showing the relative hybridization rate for three Sar variants of phage P22 (left panel); and the structure of the sar region (right panel). Variant 3 has an intact sar and it shows 100% hybridization rate. Variant 2 has 27% of its length deleted and it shows very little hybridization. Variant 1 has 43% of its length deleted, and it shows a partial restoration of hybridization rate.
Figure 5B:
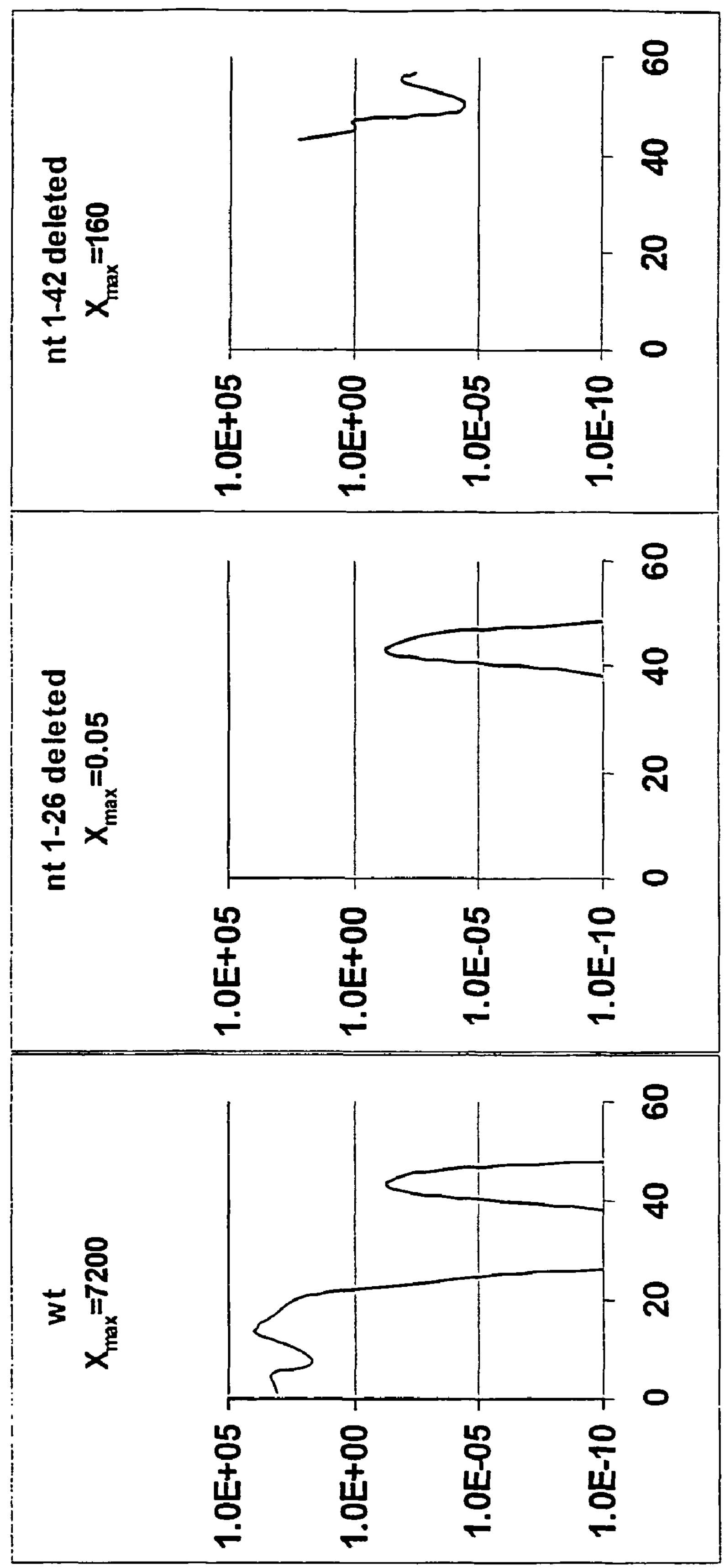
FIG. 5B shows the hybridization rate factor (x) calculated by the method of this invention for variant 3 (left panel), variant 2 (middle panel), and variant 1 (right panel), as referenced in FIG. 5A. The highest value of x is indicated at the top; those values correlate with the experimental values shown in the left panel of FIG. 5A.

In a second example, expression of the phage P22 ant gene is controlled by hybridization of an antisense RNA (sar) to ant RNA. By isolation of early intermediate dsRNA hybrids, Schaffer et al. (Schaefer and McClure, 1997) identified a nucleation site in a loop region of sar RNA that pairs with nucleotides in a short stem of ant RNA. We calculated the rate factor using Equation 14 for all regions 11 nt long and found a maximum located in the region of nucleotides 12-22 that coincides with the observed nucleation site (Schaefer and McClure, 1997). Truncation of 5' portion of sar RNA from 1 to 27 abolished the rapid annealing (Schaefer and McClure, 1997). Further deletion up to nt 43 partially restored the annealing rate. The maximum calculated rate factor correlated with the hybridization rate changes observed (FIG. 5).

Example 3

Figure 6:
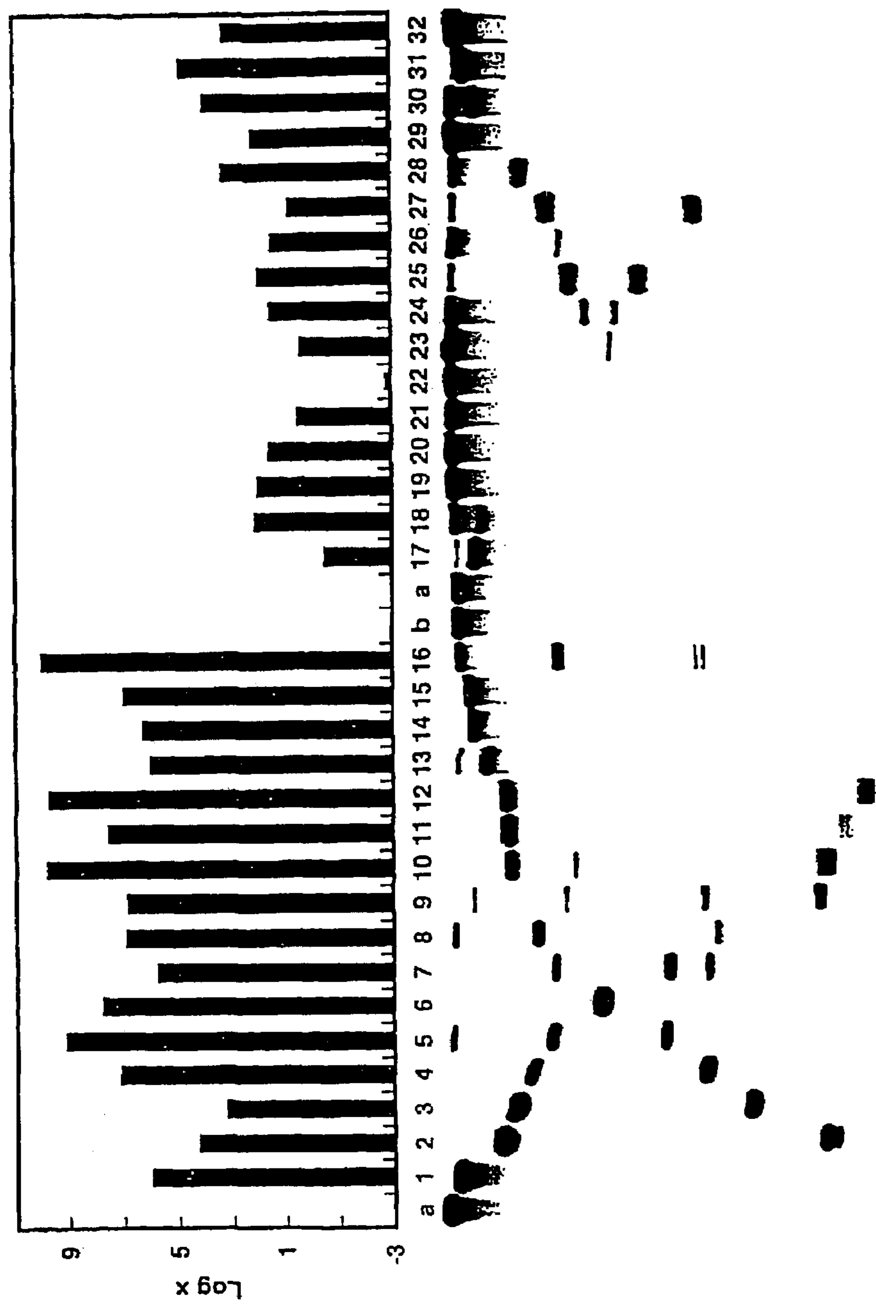
FIG. 6 illustrates RNase H cleavage of HIV-1 integrase mRNA mediated by antisense oligonucleotides.

Identification of Accessible Sites for Antisense ODN Hybridization to HIV-1 Integrase mRNA As a test for the ability of the rate factor (x in equation 14) to be used as a predictor of target site hybridization, we examined 32 sites within HIV-1 integrase mRNA that had values of x ranging from $10^{-2}$ to $10^{8}$. We prepared antisense oligodeoxynucleotides (ODNs) complementary to each site and incubated each oligonucleotide with radioactively labeled integrase mRNA and RNase H in the presence of 0.45 mM $MgCl_2$. All reactants were added at the same time, and the incubation time was limited; thus the quasi-steady-state approximation applied. Radioactive mRNA, transcribed in vitro, was incubated with individual oligonucleotides and RNase H in 0.45 mM $MgCl_2$ for 13 min. The target RNA (935 nt) and the cleavage products were separated by gel electrophoresis and detected with a PhophoImager (bottom portion of figure). The rate factor calculated for each site is shown at the top of the corresponding lane of FIG. 6. Oligonucleotides are arbitrarily numbered. The letter "a" indicates that no oligonucleotide was added, and the letter "b" indicates that an irrelevant oligonucleotide was added. Target sites calculated to have high a value for the rate factor produced distinct product fragments. Sites having low rate factor produced little distinct product. When the amount of RNA cleaved was used as a measure of hybridization, the method of this invention (Equation 14) was reliable at identifying the most favorable sites (FIG. 7*a*). Of the 17 sites having a high rate factor ($x>10^4$), all were experimentally favorable (less than 25% of the target RNA remained uncleaved). Of the 4 sites having a low factor ($x<10^2$), none exhibited substantial hybridization (greater than 60% of the target RNA remained uncleaved). Sites that had a intermediate rate factor ($10^2<x<10^4$) showed scattered results in what appears to be a sharp transition between favorable and non-favorable sites. We conclude that the rate factor, x, predicts which sites will be most favorable.

Figure 7:
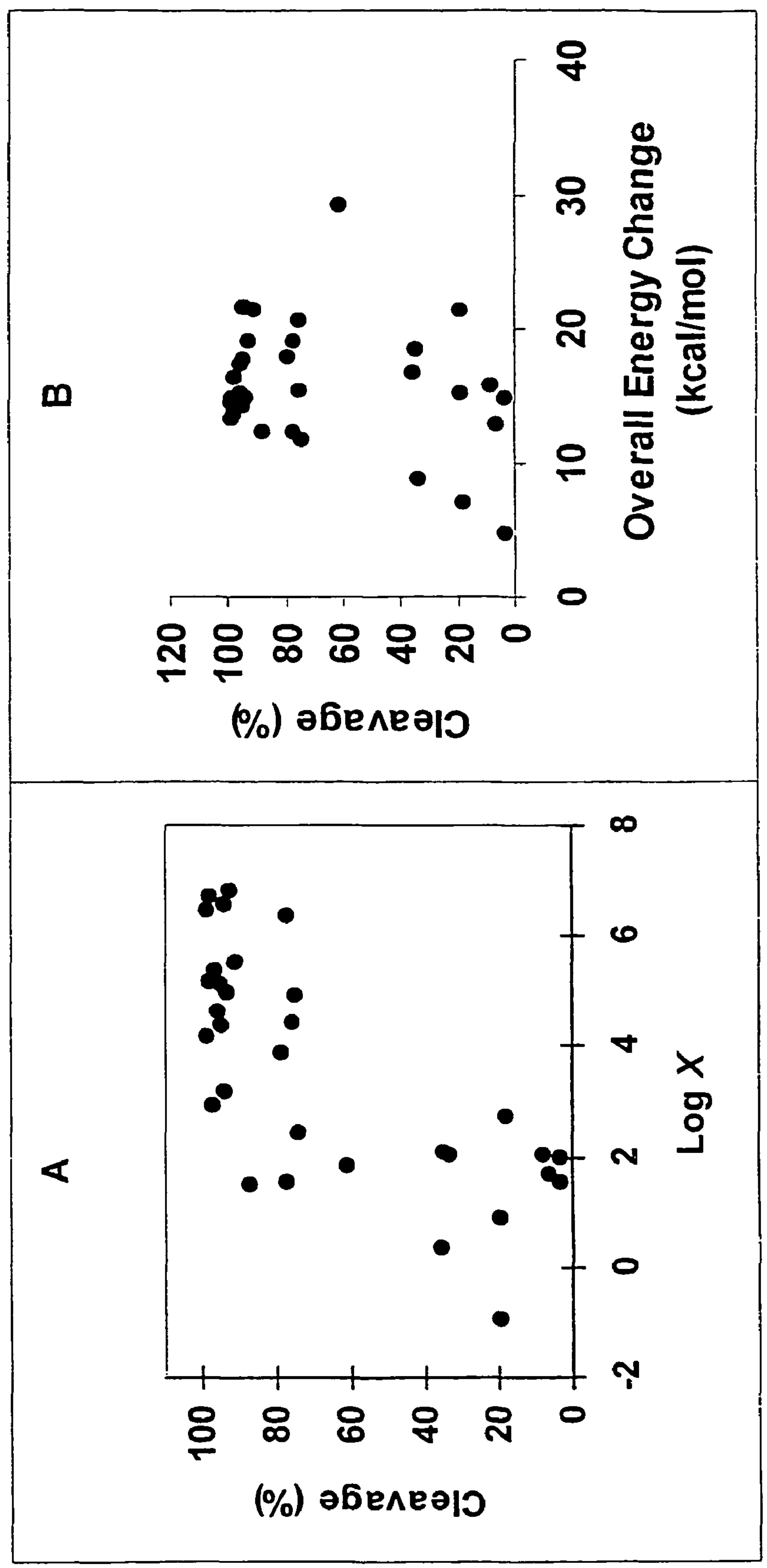
FIG. 7 illustrates the relationship between predicted and the experimental hybridizability of HIV-1 integrase mRNA. Panel A utilizes the method of this invention. Panel B utilizes the method of Mathews et al. (1999a).
Figure 8:
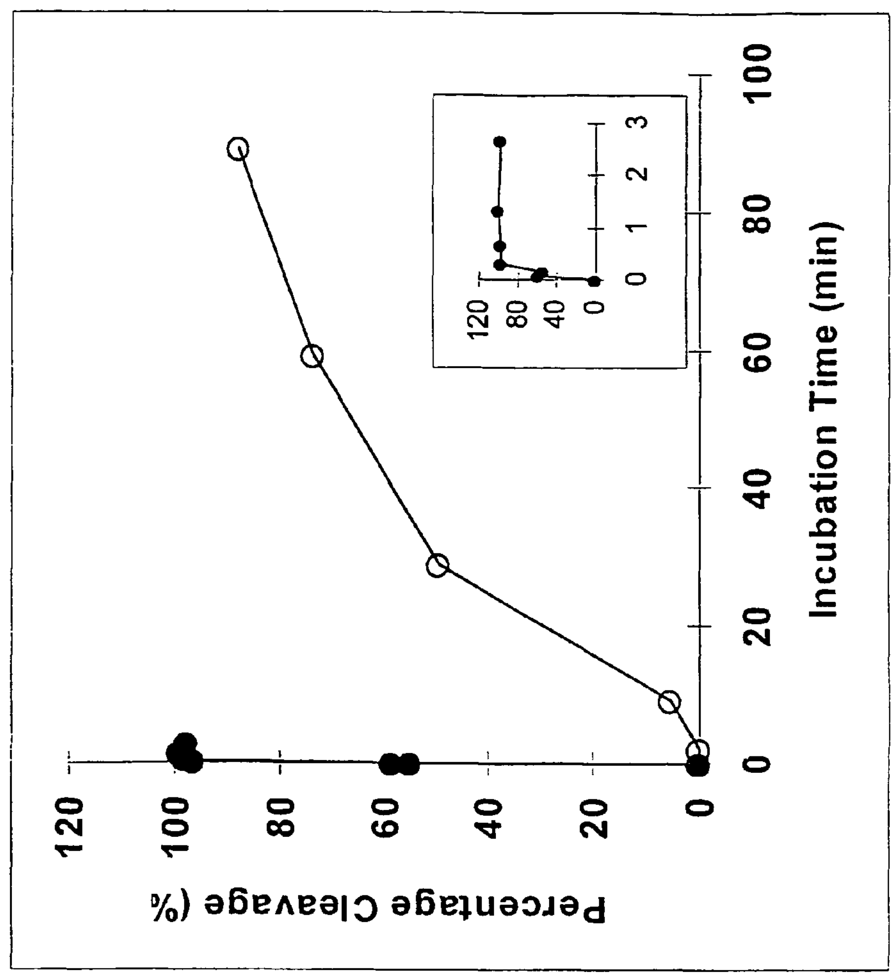
FIG. 8 shows the time course of RNase H cleavage of HIV-1 int mRNA-antisense oligonucleotide hybrids formed at the most accessible (filled circles) or least accessible (open circles) site.

Since the values of x for the 32 sites spanned many orders of magnitude, while the fraction of target RNA remaining uncleaved had only a 30-fold range, we suspected that the single time-point assay used to obtain the data shown in FIG. 7 was relatively insensitive to differences in hybridization rate. To test this idea, hybridization after various incubation times was measured using the RNase H assay for the sites having the highest and the lowest rate factors (#11 and #19 in FIG. 6). A 200-fold difference was found for cleavage rate in the quasi-linear region of the curves (FIG. 8). Oligonucleotides complementary to the most accessible site (#11 in FIG. 6, filled circles) or the least accessible site (#19 in FIG. 6, open circles) were incubated with int mRNA and RNase H in 0.45 mM $MgCl_2$ for the indicated times. The inset shows results for the most favorable site over a narrow range of incubation time. As our measurement more closely approximates initial rate, the experimental difference between favorable and unfavorable sites increases.

Example 4

Correlation between Rate Factor and Published Antisense-mRNA Hybridization

Figure 3:
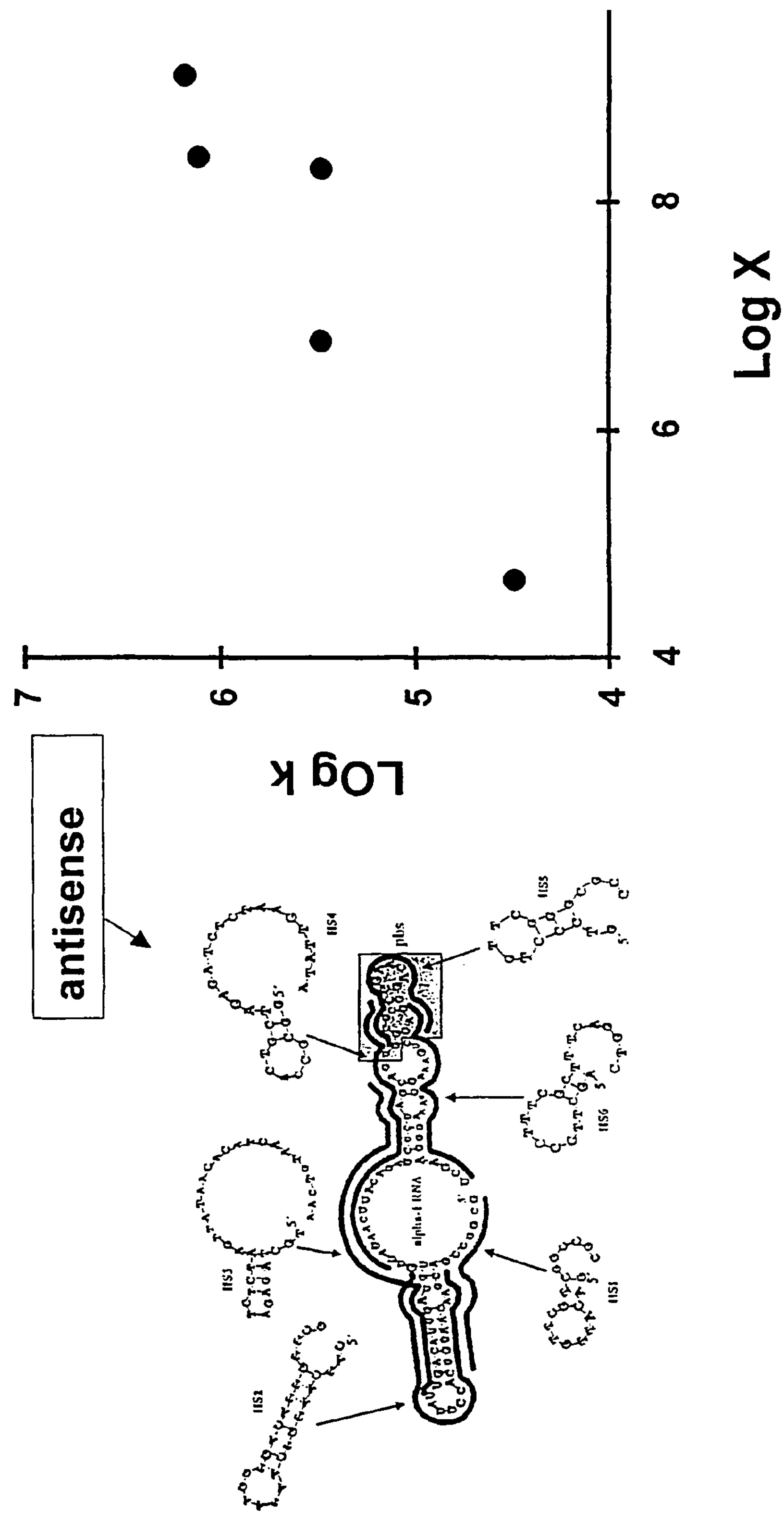
FIG. 3 is a drawing that describes hybridization of antisense oligonucleotides to a short HIV1 target RNA (SEQ ID NO:1) the secondary structure of the target RNA is shown at left, with the structures and locations of hybridization for six antisense oligonucleotides (HS1, SEQ ID NO:2; HS52, SEQ ID NO:3; HS3, SEQ ID NO:4; HS4, SEQ ID NO:5; HS5, SEQ ID NO:6; HS6, SEQ ID NO:7) shown around it; at the right is a plot showing a comparison of calculated binding rate constant for small regions using Equation 14 (x) to measured hybridization initiation rate (k) for antisense RNA oligonucleotide and HIV-1 RNA.

As a test for the generality of Equation 14, we examined the relationship between the rate factor, x, and hybridization of ODNs to sites in acetylcholinesterase mRNA (Birikh et al., 1997). In this experiment mRNA was hybridized to a pool of 10-nucleotide-long random-sequence antisense oligodeoxynucleotides. The oligonucleotides had been allowed to bind mRNA in the presence of RNase H, and the most readily hybridized regions, which were degraded by RNase H, were then revealed by gel electrophoresis. By examining the published data, we identified favorable sites (arrows, FIG. 9). Experimentally favorable sites (nucleotide positions 1,000 to 1,700) were identified from gel electrophoresis of RNase H-mediated cleavage following antisense oligonucleotide-mRNA hybridization (FIG. 3 in Birikh et al., 1997). Calculated rate factors (x) for 10-nucleotide-long antisense DNAs (solid line) are plotted against the 5' positions of antisense binding sites in acetylcholinesterase mRNA. The arrow labeled "•" indicates an experimentally favorable site predicted to be unfavorable.

Figure 9:
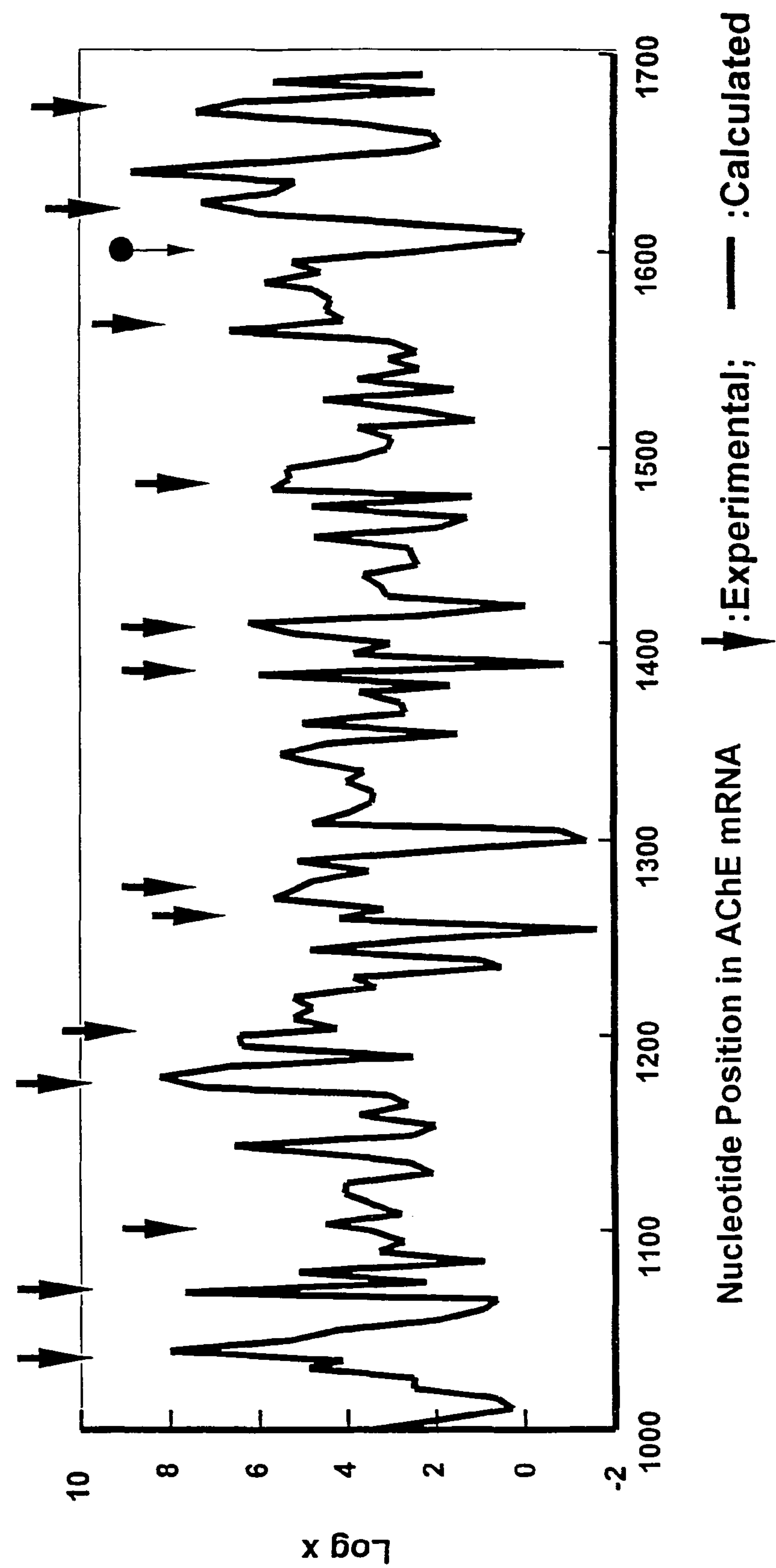
FIG. 9 illustrates the correlation between calculated rate factor and measured hybridization for antisense oligodeoxynucleotide-mRNA interaction with human acetylcholinesterase mRNA.

We also calculated the rate factor (x) for all sites in the same region of acetylcholinesterase mRNA, five nucleotides apart (trace, FIG. 9). The arrows align with peaks in the trace (FIG. 9). About half of the sites calculated to have $x>10^4$ were identified experimentally as being favorable. Similarly, 85% of the favorable sites identified experimentally were found to have a rate factor greater than $10^4$. Only one experimentally favorable site was missed by the calculation. Similar results (not shown) were obtained for mRNA of the multidrug resistance gene (Ho et al., 1996), the angiotensin type-1 receptor gene (Ho et al., 1998), murine c-myb mRNA (Jarvis et al., 1996), and fragments of Hepatitis C Virus genomic RNA (Lima et al., 1997). Thus, for seven species of RNA rate factor calculations using Equation 13 identified sites that were experimentally favorable.

Example 5

Intracellular System for Measuring Anti-Tat Activity of Antisense ODNs

In order to measure the inhibitory effect of antisense ODNs on Tat expression, three nucleic acid species were delivered to cultured human cells by transfection: an ODN, vector p731 which expresses GFP regulated by the HIV-1 LTR, and vector pCV1 which expresses HIV-1 Tat.

Human cell line was co-transfected with two plasmids and either control (panel A) or antisense (panel B) oligodeoxynucleotides. One of the plasmids expresses a green fluorescence protein (GFP) under control of HIV-1 LTR and the other expresses HIV-1 Tat. Tat protein interacts with the tar site in the transcript of GFP expressing plasmid, inducing fluorescence (panel A). When a functional ODN binds the tat mRNA, tat expression is inhibited and a lower fluorescence is observed as a background (panel B).

Figure 10:
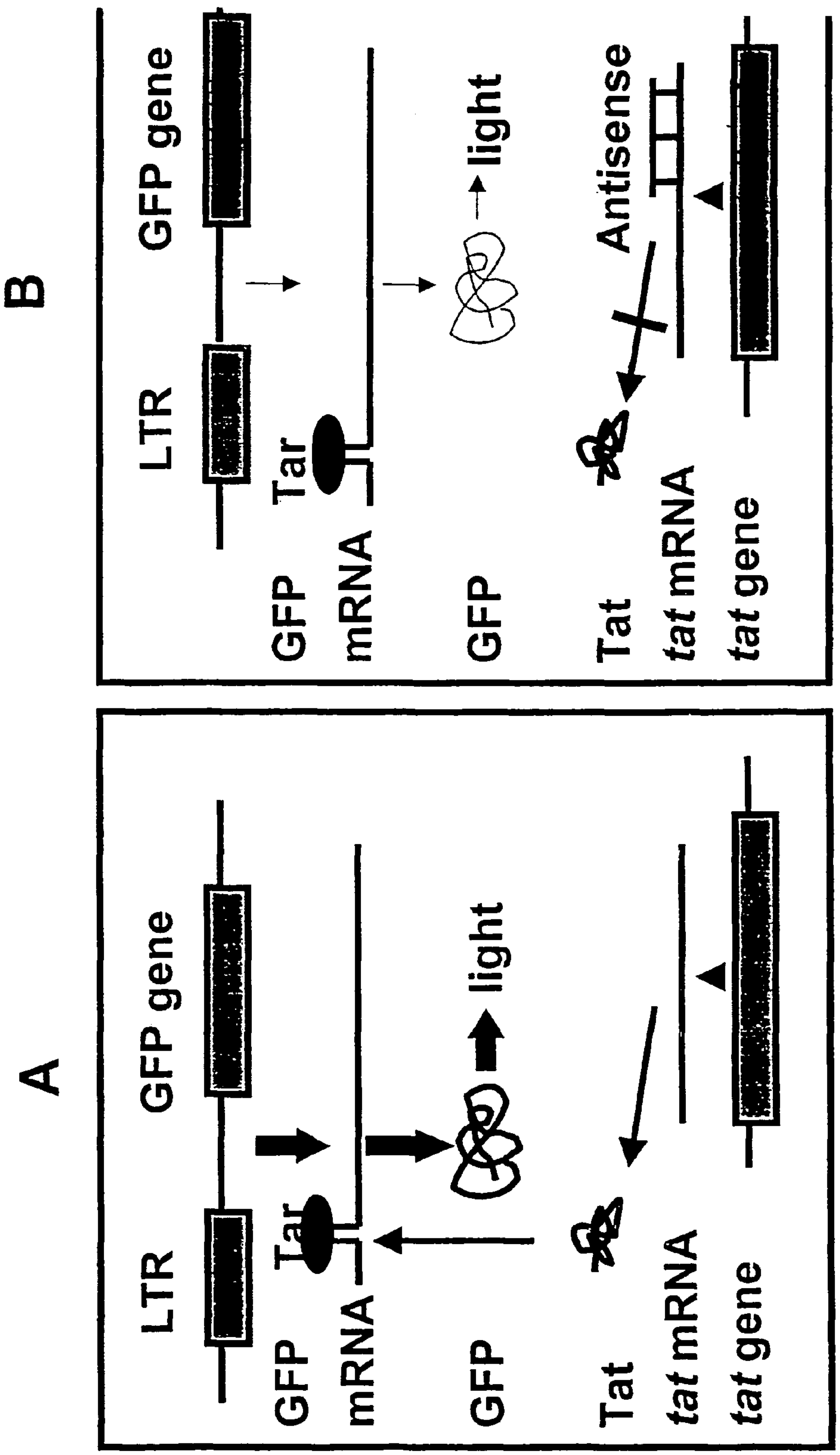
FIG. 10 shows the assay system used to determine the inhibitory effect of antisense ODNs on HIV-1 tat expression.

In this system (FIG. 10), transient expression of GFP, which was stimulated 10-fold by Tat protein, was taken as an indication of tat mRNA concentration. Attack of tat mRNA by an ODN was expected to reduce the amount of Tat and therefore decrease fluorescence.

The system was optimized, and a range was identified in which the fluorescence response was linear with respect to the amount of Tat-encoding plasmid present during transfection, which we assumed to be proportional to the amount of Tat present. The capacity of the transfection reagent FuGene™6 was found to be 2 μg DNA per 3 μl reagent, which was slightly lower than indicated by the manufacturer. Fluorescence showed a maximum at a cell density of $0.35\times10^6$ cells/ml, and it reached a maximum after 24-30 hrs incubation following transfection. Fluorescence responded linearly to concentrations of pCV1 up to 0.3 μg/well (35 mm diameter) delivered to cells along with p731 at 0.5 μg/well.

Materials and methods: p731 is a derivative of expression vector pcDNA3.1 /Zeo(−) (Invitrogen Carlsbad, Calif.) in which the green fluorescent protein (GFP) gene was inserted into the multicloning site. The promoter Pcmv was replaced with the HIV-1 LTR (nt 313-536 GenBank acc #: 03455). Thus GFP gene expression is greatly increased by the presence of the HIV-1 Tat protein.

pCV1, which constitutively transcribes tat mRNA, is described (Arya et al., 1985). The tat cDNA in pCV1 extends from nt 606 to 1265 (GenBank acc K03455).

Oligonucleotides were synthesized by Integrated DNA Technology, Inc. (Coralville, Iowa). Those used for transfecting human cells were phosphorothioates modified.

Human cell line 293 was used to transiently express the GFP and tat genes. This cell line is an adenovirus-transformed human embryo kidney cell line containing and expressing the early regions of adenovirus. They complement the growth of E1-deficient adenovirus mutants and vectors. Cells were grown in RPMI 1640 basic medium (BioWhittaker, Walkersville, Md.) with addition of 10% heat-inactivated fetus bovine serum (FBS), 50 u/ml of penicillin, 50 μg/ml of streptomycin, and 4 mM glutamine. FBS, glutamine, and antibiotics were filtered through a 0.2 μm sterile filter before addition to RPMI 1640 medium.

Prewarmed RPMI medium (6 ml) was inoculated with $10^6$ cells of human cell line 293 and incubated at 37° C. in a 100×20 mm dish (culture area 55 $cm^2$). When growth was confluent, growth medium was removed, and cells were washed with 6 ml PBS. The cells were then removed from the walls of the dish with trypsin treatment and resuspended at a concentration of $0.35\times10^6$ cells/ml. 2 ml cells were transferred into each well (60 mm in diameter, 21 $cm^2$ area) of 6-well plastic culture plates (Fisher, Springfield, N.J.). After 24-hour incubation at 37° C., cells were transfected with plasmids and oligonucleotides.

For transfection, a mixture of 6 μl FuGene™ 6 (Boehringer Mannheim) and 100 μl RPMI medium lacking FBS was incubated at room temperature for 5 min and then was added dropwise to an Eppendorf tube containing the DNA to be transferred into cells. The resulting conjugates were incubated at room temperature for 15 min and then added to 293 cells in a well of a 6-well plate. The plates were incubated for 24-30 hours during which time expression of HIV-1 Tat occurred.

To quantify the fluorescence due to the presence of GFP, growth medium was removed and cells were washed with 2 ml PBS. 350 μl lysis buffer containing 50 mM Tris.HCl (pH 8.0), 1% NP40, 0.02% $NaN_3$, 100 μg/ml PMSF, and 1 μg/ml Aprotinin (Sigma) was added per well to break the cells. After incubation for 15 min on ice, the lysate was transferred to a centrifuge tube, and cellular debris was removed by centrifuation for 5 min at full speed in a microcentrifuge. The supernatant fluid (150 μl) was transferred to a well of a MicroFluorescence plate (Dynatech) for measurement of fluorescence using a fluorescence reader with an excitation wavelength of 485 nm and an emission wavelength of 535 nm.

As a template for synthesis of tat mRNA, tat cDNA from plasmid pCV1 was subcloned into plasmid pUC19 after being amplified by PCR using two primers:

```
pCV1L
(5'CTGCAGGAATTCTAATACGACTCACTATAGCTTTTAGTCAGTGTGGA
AAATCTCTAGC),

and

pCV1R
(5'CTGCAGGAATTCGCACTCAAGGCAAGCTTTATTGAGGCTT).
```

PCR generated a T7 promoter upstream of the gene and an EcoRI site at each end. The resulting plasmid, pUCtat, served as a template for runoff transcription after linearization by EcoRI digestion.

Example 6

Figure 11:
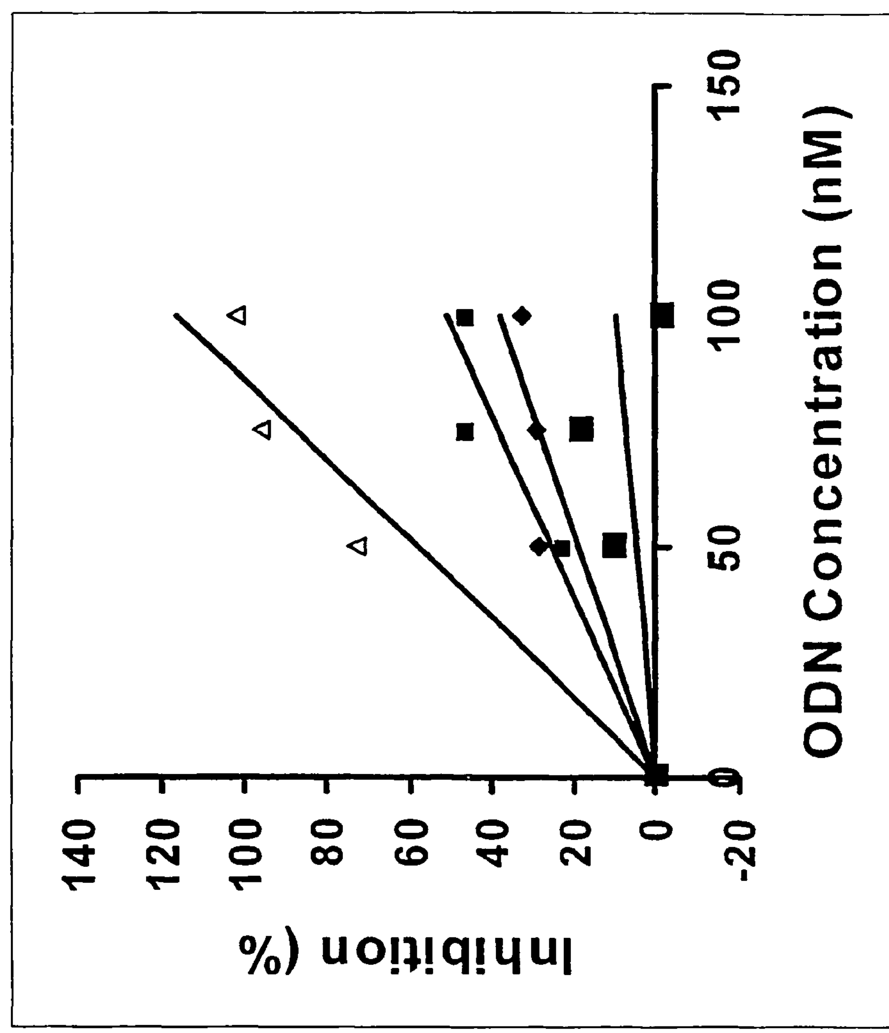
FIG. 11 illustrates the concentration effect of antisense ODN on inhibition of tat expression in cultured human cells.

Correlation between Intracellular Inhibition of GFP by Anti-tat Oligodeoxynucleotides and Calculated Hybridization Rate Factor To determine how well the calculated rate factor corresponds to intracellular antisense activity, we first measured the effect of various concentrations of 16 ODNs on tat expression (see Table 3 for nucleotide sequences). For each antisense ODN, increasing the concentration up to 100 nM (0.2 nmole/well) decreased fluorescence (representative examples are shown in FIG. 11). In these experiments, human cells of the 293 cell line were grown in wells of 6 well-plates and transfected with 0.5 µg GFP plasmid DNA, 0.3 µg Tat plasmid DNA, and 0.1 µg pBR322 DNA along with various amount of antisense ODN as indicated. Scrambled ODN was added to keep the total ODN constant at 100 nM or 0.2 nmole/well.

The slope of lines such as those in FIG. 11 were then plotted against calculated values of the hybridization rate factor (x) in Equation 13 for each of the 16 ODNs. The relationship between rate factor and antisense activity, shown in FIG. 12, had a correlation coefficient of 0.8 ($p<0.001$). In these experiments, Human 293 cells in wells of 6-well plates were transfected with individual ODN at concentrations as indicated in the FIG. 11 along with 0.5 µg/well p731 (GFP), 0.3 µg/well pCV1, and 0.1 µg/well pBR322. The transfectants were incubated at 37° C. for 30 hrs. Dosage dependent rate of fluorescence decrease (curve slope) as an inhibitory indicator was averaged over three sets of experiments and was plotted versus calculated hybridizability. These data indicate that intracellular hybridization of antisense ODNs to many regions of an mRNA can be modeled by considering only RNA secondary structure.

TABLE 3

Antisense oligodeoxynucleotides used in experiments

| ID # | Pairing region[a] | Nucleotide sequence[b] | SEQ ID NO: | Log x[c] | Inhibitory effect[d] (1/nm) |
|---|---|---|---|---|---|
| 8150 | 140-159 | CTGCTATGTC GACACCCAAT | 10 | 6.2 | 0.47 |
| 8151 | 194-213 | GTCTAGGATC TACTGGCTCC | 11 | 6.5 | 0.67 |
| 8152 | 231-250 | GTTTTAGGCT GACTTCCTGG | 12 | 3.1 | 0.54 |
| 8153 | 285-304 | AAACAAACTT GGCAATGAAA | 13 | 3.4 | 0.30 |
| 8154 | 210-229 | TGCTTCCAGG GCTCTAGTCT | 14 | 4.7 | 0.56 |
| 8156 | 59-78 | GAGCTCCTCT GGTTTCCCTT | 15 | 6.6 | 0.55 |
| 8157 | 185-204 | CTACTGGCTC CATTTCTTGC | 16 | 6.5 | 0.63 |
| 8158 | 257-276 | TTTTACAATA GCAATTGGTA | 17 | 3.4 | 0.19 |
| 8159 | 293-312 | TTGTTATGAA ACAAACTTGG | 18 | 1.7 | 0.23 |
| 8160 | 311-330 | AGGAGATGCC TAAGGCTTTT | 19 | 6.2 | 0.70 |
| 8161 | 467-486 | GATCTGTCTC TGTCTCTCTC | 20 | 8.4 | 1.81 |
| 8162 | 1004-1023 | CCACCTCCTC CTCCTCTTGT | 21 | 8.5 | 0.73 |
| 8179 | 775-794 | TTATTCTTCT AGGTATGTGG | 22 | 8.1 | 0.42 |
| 8180 | 975-994 | CAGGCACAAG CAGCATTGGT | 23 | 0.1 | 0.49 |
| 8182 | 1208-1227 | ATCTGACCCC TGGCCCTGGT | 24 | 0.5 | 0.18 |
| 8183 | 1240-1259 | TAGCTTGTAG CACCATCCAA | 25 | -2.2 | 0.03 |
| 8177 | Scrambl | CTTACACTGC CATTGCTACA | 26 | | |

[a]Numbering system for nucleotide position is as reference (Arya et al., 1985).
[b]All nucleotides used for transfection are phosphorothioate modified.
[c]Accssibility index x was calculated as described in Methods and Materials
[d]Average slope of the dosage curve (FIG. 11) is taken as inhibitory effect.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, it is contemplated that the new methods can be used to create a library of best sites for every gene in a given genome.

What is claimed is:

1. A method for identifying at least one target site of an RNA molecule for attack with an antisense RNA nucleic acid, the method comprising:

(a) for all short pairing regions in an RNA molecule, said short pairing regions having a selected length in the range of 11 to 20 nucleotides (i) calculating the melting energy (ΔGm) required to convert each of said short pairing regions of the RNA molecule to a single-stranded state;

(ii) calculating the energy gain ($\Delta G_d$) resulting from hybridization of each of said short pairing regions to an antisense RNA nucleic acid; and (iii) calculating rate factor x wherein $$x = \frac{1}{Ce^{\Delta G_m/RT} + e^{\Delta G_d/RT}},$$

wherein C is a proportionality constant, R is the universal gas constant and T is temperature;

(b) identifying at least one region that has a maximal value of rate factor x; and (c) displaying the identified at least one region that has a maximal value of rate factor.

2. A device for identifying target sites of RNA molecules for attack with antisense RNA nucleic acids, the device comprising a computer having an executable program for carrying out the process steps of the method of claim 1 and displaying the identified at least one region that has a maximal value of rate factor.

* * * * *